(12) United States Patent
Adachi et al.

(10) Patent No.: US 10,775,357 B2
(45) Date of Patent: Sep. 15, 2020

(54) GAS SENSOR

(71) Applicant: NGK INSULATORS, LTD., Nagoya-shi, Aichi (JP)

(72) Inventors: Yosuke Adachi, Nagoya (JP); Tetsuya Ishikawa, Kasugai (JP); Jumpei Tanaka, Toyohashi (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 15/623,452

(22) Filed: Jun. 15, 2017

(65) Prior Publication Data

US 2017/0363599 A1 Dec. 21, 2017

(30) Foreign Application Priority Data

Jun. 17, 2016 (JP) .................. 2016-121005

(51) Int. Cl.
*G01M 15/10* (2006.01)
*G01N 33/00* (2006.01)

(52) U.S. Cl.
CPC ....... *G01N 33/0009* (2013.01); *G01M 15/102* (2013.01)

(58) Field of Classification Search
CPC ............ G01N 33/0009; G01N 1/2252; G01M 15/102
See application file for complete search history.

(56) References Cited

U.S. PATENT DOCUMENTS

| 2008/0156644 A1 | 7/2008 | Suzuki et al. |
| 2015/0101394 A1* | 4/2015 | Fujita .................. G01N 27/4077 73/23.31 |
| 2016/0076919 A1 | 3/2016 | Murakami et al. |

FOREIGN PATENT DOCUMENTS

| JP | 2008-164411 A | 7/2008 |
| WO | 2014192945 A1 | 12/2014 |

* cited by examiner

*Primary Examiner* — Lisa M Caputo
*Assistant Examiner* — Alex T Devito
(74) *Attorney, Agent, or Firm* — Global IP Counselors, LLP

(57) ABSTRACT

An inner protective cover 130 of a gas sensor forms an element-chamber inlet 127 having a first outside opening 128*a*, a second outside opening 128*b*, and an element-side opening 129. The second outside opening 128*b* is disposed such that the path of a measurement-object gas from the first outside opening 128*a* to the element-side opening 129 of the element-chamber inlet 127 communicates in the middle thereof with a first gas chamber 122, and that there is a path shorter than the shortest path of the measurement-object gas extending from an outer inlet 144*a* through the first outside opening 128*a* to a gas inlet 111.

8 Claims, 13 Drawing Sheets

CENTRAL AXIS

GAS SENSOR

BACKGROUND OF THE INVENTION

1. Field of the Invention

The present invention relates to a gas sensor.

2. Description of the Related Art

Gas sensors have been known, which detect the concentration of a predetermined gas, such as NOx or oxygen, in a measurement-object gas, such as an exhaust gas of a car. For example, PTL 1 describes a gas sensor that includes an outer protective cover having an outer gas hole, and an inner protective cover formed in the shape of a cylinder with a bottom, disposed between the outer protective cover and a sensor element, and configured to cover the front end of the sensor element. In the gas sensor described in PTL1, the inner protective cover forms a gas flow passage in the path of a measurement-object gas from the outer gas hole to a gas inlet of the sensor element. The gas flow passage extends from the back side toward the front side of the sensor element and opens toward a space having the gas inlet disposed therein. PTL 1 states that with this configuration, it is possible to ensure both responsiveness in gas concentration detection and heat retaining properties of the sensor element.

CITATION LIST

Patent Literature

PTL 1 WO 2014/192945 A1

SUMMARY OF THE INVENTION

The responsiveness in gas concentration detection varies depending on the velocity of the measurement-object gas flowing around the gas sensor. The responsiveness tends to be low when the flow velocity is low (e.g., 4 m/s or less).

The present invention has been made to solve the problem described above. A primary object of the present invention is to reduce loss of responsiveness when a measurement-object gas flows at low velocity.

The present invention takes the following measures to achieve the primary object described above.

A gas sensor according to the present invention includes a sensor element having a gas inlet that introduces a measurement-object gas into the sensor element and capable of detecting a concentration of a predetermined gas in the measurement-object gas that has flowed through the gas inlet into the sensor element; an inner protective cover containing a sensor element chamber therein having a front end of the sensor element and the gas inlet disposed therein, the inner protective cover having one or more element-chamber inlet serving as an entrance to the sensor element chamber; and an outer protective cover having one or more outer inlet serving as an entrance for the measurement-object gas from the outside, the outer protective cover being disposed outside the inner protective cover. The outer protective cover and the inner protective cover form a first gas chamber as a space therebetween. The first gas chamber is at least part of a flow passage of the measurement-object gas between the outer inlet and the element-chamber inlet. The inner protective cover forms the element-chamber inlet having a first outside opening adjacent to the first gas chamber, an element-side opening adjacent to the sensor element chamber and located downstream of the first outside opening in a front direction which is from a back end toward the front end of the sensor element, and a second outside opening disposed such that a path of the measurement-object gas from the first outside opening to the element-side opening communicates in the middle thereof with the first gas chamber and that there is a path shorter than the shortest path of the measurement-object gas extending from the outer inlet through the first outside opening to the gas inlet.

In the gas sensor described above, the measurement-object gas around the gas sensor flows in through the outer inlet of the outer protective cover, passes through the first gas chamber and the element-chamber inlet, and reaches the gas inlet of the sensor element. Flow passages along which the measurement-object gas passes through the element-chamber inlet include a flow passage extending through the first outside opening and a flow passage extending through the second outside opening. The second outside opening is disposed such that there is a path shorter than the shortest path of the measurement-object gas extending from the outer inlet through the first outside opening to the gas inlet. In other words, the length of the shortest path of the measurement-object gas extending from the outer inlet through the second outside opening to the gas inlet (also referred to as a shortest second path length P2) is smaller than the length of the shortest path of the measurement-object gas extending from the outer inlet through the first outside opening to the gas inlet (also referred to as a shortest first path length P1). With the second outside opening, even when the measurement-object gas flows at low velocity, the measurement-object gas that has flowed in through the outer inlet passes through the second outside opening and can reach the gas inlet in a relatively short time. It is thus possible to reduce loss of responsiveness when the measurement-object gas flows at low velocity. When the measurement-object gas flows at high velocity or rate, since there is a flow passage extending through the first outside opening as well as a flow passage extending through the second outside opening, the flow velocity or rate of the measurement-object gas passing through the element-chamber inlet is not easily reduced. Therefore, for example, as compared to the case where there is no first outside opening, the loss of responsiveness when the measurement-object gas flows at high velocity can also be reduced.

In the gas sensor according to the present invention, the shortest second path length P2 is preferably from 5.0 mm to 11.0 mm. If the shortest second path length P2 is 11.0 mm or less, the effect of reducing the loss of responsiveness at low flow velocity can be more reliably achieved. If the shortest second path length P2 is 5.0 mm or more, problems which may arise when the shortest second path length P2 is too small can be reduced. Examples of such problems are that external poisoning material or water flowing in through the outer inlet easily reaches the sensor element, and that the sensor element is easily cooled by the measurement-object gas. The shortest second path length P2 is preferably 10.5 mm or less, more preferably 10.0 mm or less, more preferably 9.5 mm or less, still more preferably 9.0 mm or less, and even more preferably 8.5 mm or less. The smaller the shortest second path length P2, the higher the effect of reducing the loss of responsiveness at low flow velocity. The shortest second path length P2 may be 6.0 mm or more. The shortest first path length P1 may be any length greater than the shortest second path length P2. For example, the shortest first path length P1 may be greater than 11.0 mm, greater than or equal to 13.0 mm, or smaller than or equal to 20.0 mm. The difference between the shortest first path length P1 and the shortest second path length P2 (P1−P2) may be 3 mm or more, 5 mm or more, or 6 mm or more. The difference (P1−P2) may be 10 mm or less.

In the gas sensor according to the present invention, the second outside opening does not necessarily need to open toward a region extending from the outer inlet. With this configuration, even if water enters the interior of the outer protective cover through the outer inlet, the water does not easily flow in through the second outside opening. It is thus possible to prevent water from easily adhering to the sensor element and improve heat retaining properties of the sensor element.

In the gas sensor according to the present invention, the outer protective cover may include a cylindrical barrel part having a side portion and a bottom portion; the outer inlet may include a vertical hole disposed in the bottom portion of the barrel part of the outer protective cover; and when the vertical hole, the second outside opening, and a central axis of the outer protective cover are projected onto a plane perpendicular to the central axis, the projected vertical hole and the projected second outside opening do not necessarily need to overlap as viewed in a radial direction of the outer protective cover from the projected central axis. In this configuration, the vertical hole included in the outer inlet and the second outside opening are relatively distant in the circumferential direction of the outer protective cover. Therefore, even if water enters the interior of the outer protective cover through the vertical hole, the water does not easily flow in through the second outside opening. It is thus possible to prevent water from easily adhering to the sensor element and improve heat retaining properties of the sensor element.

In the gas sensor according to the present invention, the outer protective cover may include a cylindrical barrel part having a side portion and a bottom portion, and the side portion does not necessarily need to have the outer inlet. If the side portion of the barrel part has the outer inlet, water may easily enter the interior of the outer protective cover through the outer inlet. When the side portion does not have the outer inlet, the amount of such water entry can be reduced. In this case, at least one of the bottom portion and the corner portion on the boundary between the side portion and the bottom portion may have the outer inlet. Only the bottom portion or the corner portion may have the outer inlet.

In the gas sensor according to the present invention, the inner protective cover may form the element-chamber inlet such that the element-side opening opens in the front direction. This can prevent the measurement-object gas flowing out of the element-side opening from perpendicularly hitting the surface (except the gas inlet) of the sensor element, and can also prevent the measurement-object gas from traveling a long distance over the surface of the sensor element to reach the gas inlet. It is thus possible to reduce cooling of the sensor element. Additionally, since cooling of the sensor element is reduced by adjusting the orientation of the element-side opening, not by reducing the flow rate or velocity of the measurement-object gas inside the inner protective cover, the loss of responsiveness in gas concentration detection can be reduced. It is thus possible to ensure both responsiveness and heat retaining properties of the sensor element. Note that "the element-side opening opens in the front direction" refers to the case where the element-side opening opens in a direction parallel to the front direction of the sensor element, or the case where the element-side opening opens in a direction inclined with respect to the front direction such that it becomes closer to the sensor element with increasing distance from the back end toward the front end of the sensor element.

In the gas sensor according to the present invention, the inner protective cover may have a first cylindrical portion surrounding the sensor element, and a second cylindrical portion greater in diameter than the first cylindrical portion; the first cylindrical portion and the second cylindrical portion may form the first outside opening as an opening of a cylindrical gap between an outer periphery of the first cylindrical portion and an inner periphery of the second cylindrical portion, the opening being adjacent to the first gas chamber, and may form the element-side opening as an opening of the cylindrical gap adjacent to the sensor element chamber; and the second cylindrical portion may have the second outside opening that allows the cylindrical gap to communicate with the first gas chamber.

In the gas sensor according to the present invention, the inner protective cover may have one or more element-chamber outlet serving as an exit from the sensor element chamber; the outer protective cover may have one or more outer outlet serving as an exit for the measurement-object gas to the outside; and the outer protective cover and the inner protective cover may form a second gas chamber as a space therebetween, the second gas chamber being at least part of a flow passage of the measurement-object gas between the outer outlet and the element-chamber outlet, the second gas chamber not directly communicating with the first gas chamber. In this case, the outer protective cover may include a cylindrical barrel part having the outer inlet, and a front end portion having the outer outlet, formed in the shape of a cylinder with a bottom, and smaller in inside diameter than the barrel part, the front end portion being located downstream of the barrel part in the front direction; and the outer protective cover and the inner protective cover may form the first gas chamber as a space between the barrel part of the outer protective cover and the inner protective cover, and may form the second gas chamber as a space between the front end portion of the outer protective cover and the inner protective cover.

DETAILED DESCRIPTION OF THE INVENTION

Figure 1:
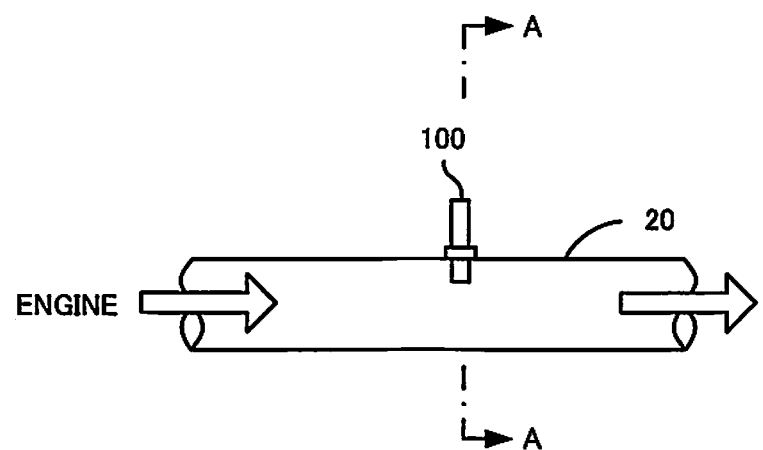
FIG. 1 is a schematic diagram illustrating a gas sensor 100 attached to a pipe 20.
Figure 2:
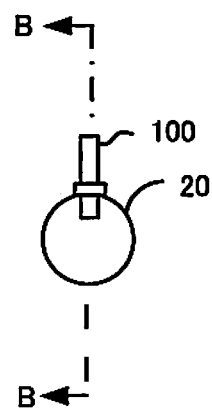
FIG. 2 is a cross-sectional view taken along line A-A of FIG. 1.
Figure 3:
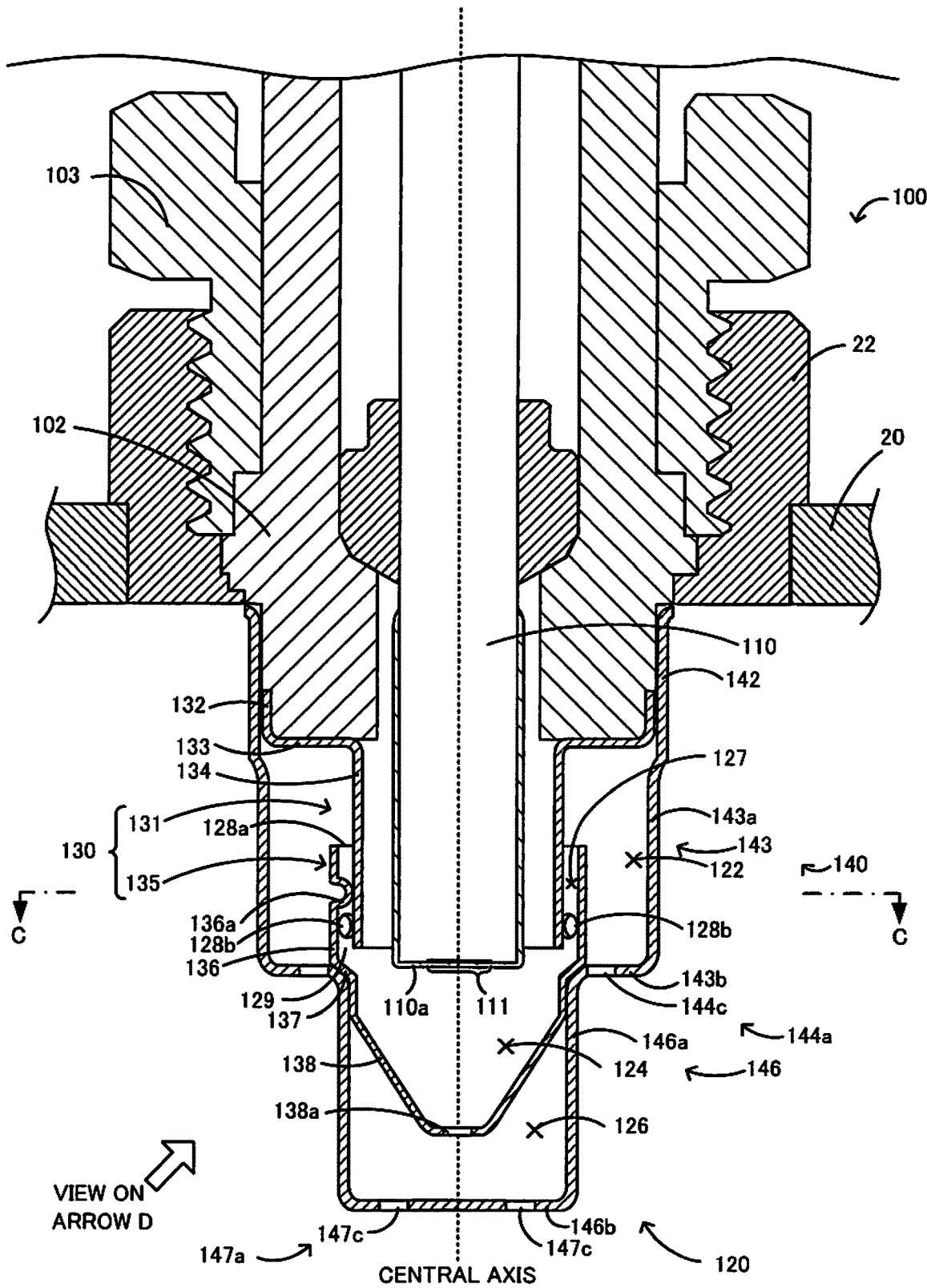
FIG. 3 is a cross-sectional view taken along line B-B of FIG. 2.
Figure 4:
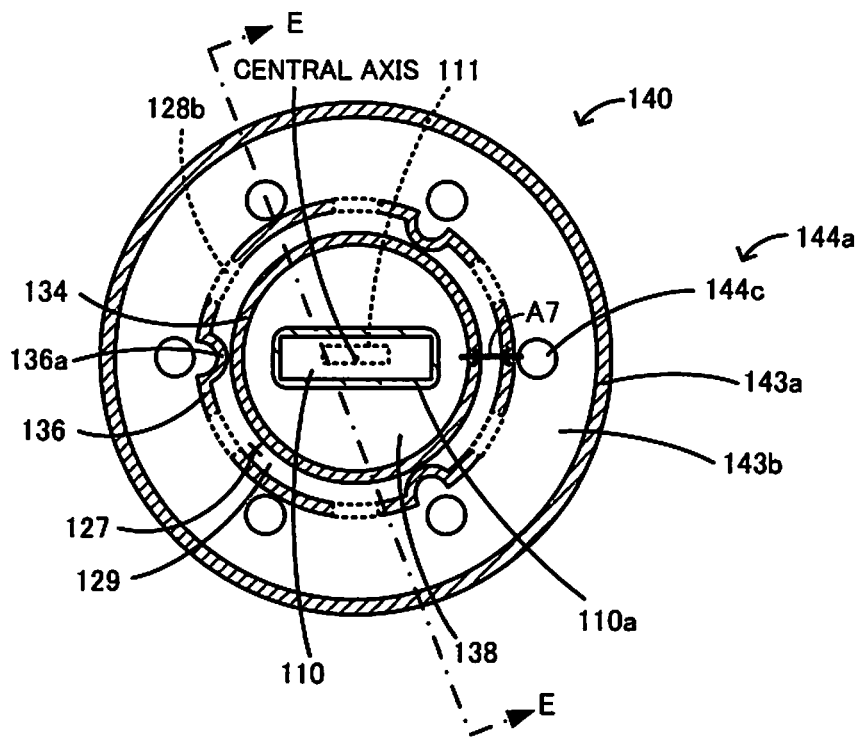
FIG. 4 is a cross-sectional view taken along line C-C of FIG. 3.
Figure 5:
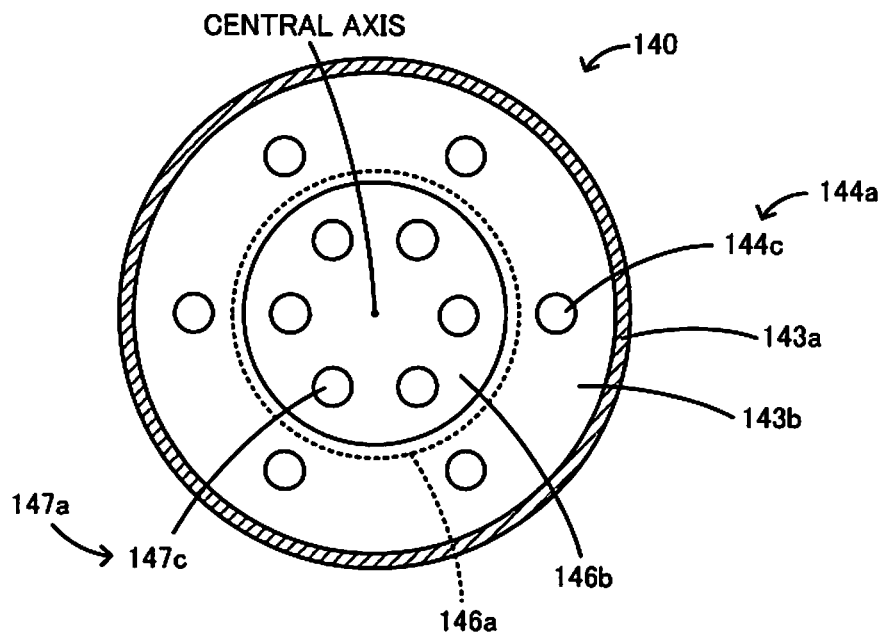
FIG. 5 is a cross-sectional view of an outer protective cover 140 taken along line C-C of FIG. 3.
Figure 6:
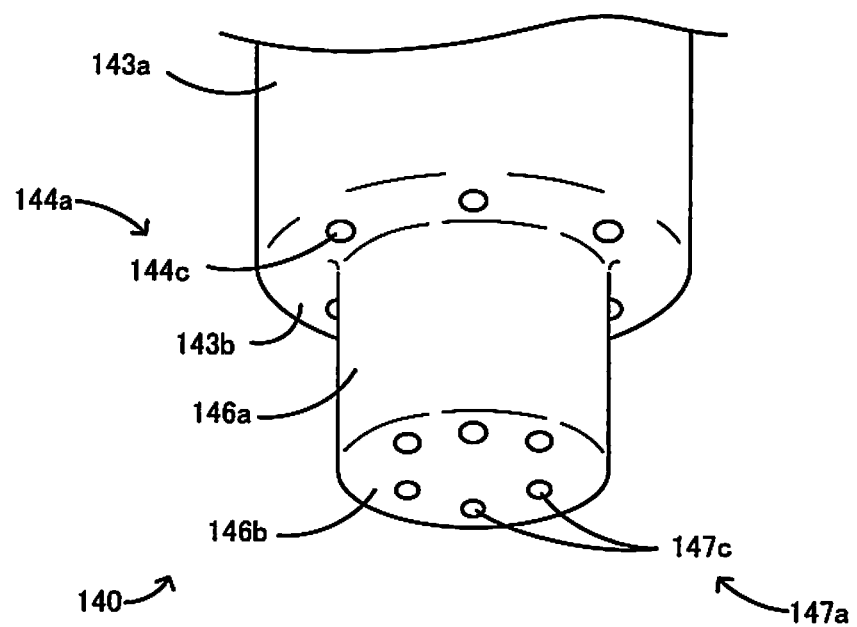
FIG. 6 is a view on arrow D of FIG. 3.
Figure 7:
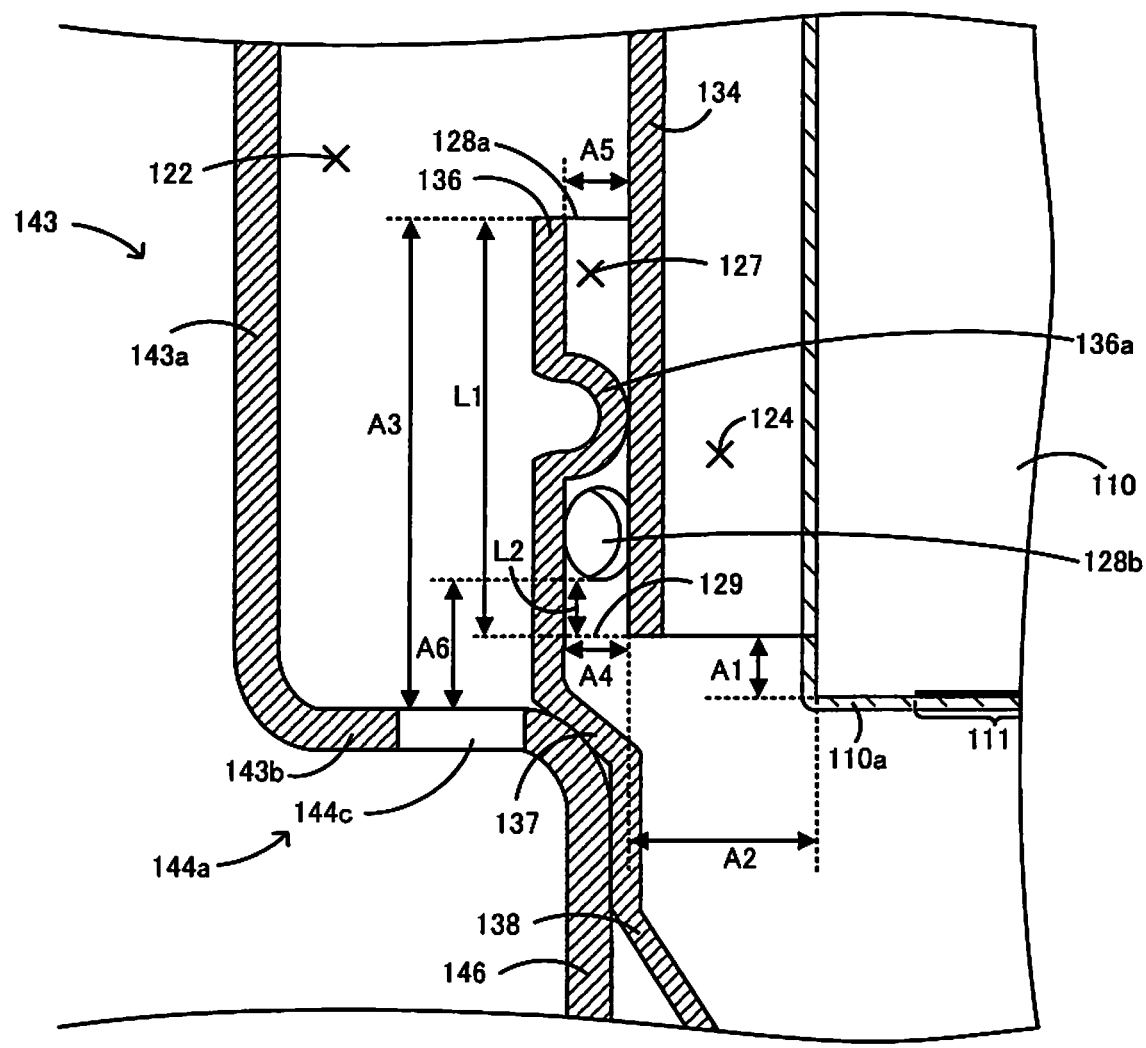
FIG. 7 is an enlarged partial cross-sectional view of an element-chamber inlet 127 and its vicinity illustrated in FIG. 3.

Embodiments for carrying out the present invention will be described using the drawings. FIG. 1 is a schematic diagram illustrating a gas sensor 100 attached to a pipe 20. FIG. 2 is a cross-sectional view taken along line A-A of FIG. 1. FIG. 3 is a cross-sectional view taken along line B-B of FIG. 2. FIG. 4 is a cross-sectional view taken along line C-C of FIG. 3. FIG. 5 is a cross-sectional view of an outer protective cover 140 taken along line C-C of FIG. 3. Note that FIG. 5 is a diagram obtained by removing a first cylindrical portion 134, a second cylindrical portion 136, an end portion 138, and a sensor element 110 from FIG. 4. FIG. 6 is a view on arrow D of FIG. 3. FIG. 7 is an enlarged partial cross-sectional view of an element-chamber inlet 127 and its vicinity illustrated in FIG. 3.

As illustrated in FIG. 1, the gas sensor 100 is attached to and inserted into the pipe 20 which is an exhaust path from an engine of a vehicle. The gas sensor 100 is configured to detect the concentration of at least one of gas components, such as NOx and $O_2$, contained in an exhaust gas (measurement-object gas) from the engine. As illustrated in FIG. 2, the gas sensor 100 is secured inside the pipe 20, with the central axis of the gas sensor 100 being perpendicular to the flow of the measurement-object gas in the pipe 20. The gas sensor 100 may be secured inside the pipe 20 such that the central axis of the gas sensor 100 is perpendicular to the flow of the measurement-object gas in the pipe 20 and is inclined by a predetermined angle (e.g., 45°) with respect to the vertical direction.

As illustrated in FIG. 3, the gas sensor 100 includes the sensor element 110 having the function of detecting the concentration of a predetermined gas in the measurement-object gas, and a protective cover 120 configured to protect the sensor element 110. Additionally, the gas sensor 100 includes a metal housing 102 and a metal nut 103 having a male-threaded outer periphery. The housing 102 is inserted in a securing member 22 welded to the pipe 20 and having a female-threaded inner periphery. Inserting the nut 103 into the securing member 22 secures the housing 102 to the inside of the securing member 22. The gas sensor 100 is thus secured inside the pipe 20. Note that the measurement-object gas in the pipe 20 flows from left to right in FIG. 3.

The sensor element 110 is a long, narrow, plate-like element having a multilayer structure of oxygen ion conductive solid electrolyte layers, such as zirconia ($ZrO_2$) layers. The sensor element 110 has a gas inlet 111 that introduces the measurement-object gas into the sensor element 110. The sensor element 110 is configured to be capable of detecting the concentration of a predetermined gas (e.g., NOx or $O_2$) in the measurement-object gas flowing in through the gas inlet 111. In the present embodiment, the gas inlet 111 opens to the front end face of the sensor element 110 (i.e., to the lower face of the sensor element 110 in FIG. 3). The sensor element 110 has a heater therein serving as a temperature regulator that heats the sensor element 110 and retains the heat in the sensor element 110. The structure of the sensor element 110 and the principle of gas concentration detection of the sensor element 110 are known and described, for example, in Japanese Unexamined Patent Application Publication No. 2008-164411. The front end (or lower end in FIG. 3) and the gas inlet 111 of the sensor element 110 are disposed in a sensor element chamber 124. Note that the direction from the back end to the front end of the sensor element 110 (i.e., the downward direction in FIG. 3) is referred to as a "front direction".

The sensor element 110 has a porous protective layer 110a thereon that covers at least part of the surface of the sensor element 110. In the present embodiment, the porous protective layer 110a is formed on five of the six faces of the sensor element 110. The porous protective layer 110a thus covers substantially the entire surface of the sensor element 110 exposed to the interior of the sensor element chamber 124. Specifically, the porous protective layer 110a covers the entire front end face (or lower face in FIG. 3) of the sensor element 110 having the gas inlet Ill. The porous protective layer 110a covers parts of the four faces connected to the front end face of the sensor element 110 (i.e., the upper, lower, right, and left faces of the sensor element 110 in FIG. 4) close to the front end face of the sensor element 110. For example, the porous protective layer 110a prevents water in the measurement-object gas from adhering to, and causing cracks in, the sensor element 110. The porous protective layer 110a also prevents an oil component contained in the measurement-object gas from adhering to an electrode (not shown) on the surface of the sensor element 110. The porous protective layer 110a is formed of a porous body, such as an alumina porous body, a zirconia porous body, a spinel porous body, a cordierite porous body, a titania porous body, or a magnesia porous body. The porous protective layer 110a can be formed, for example, by plasma spraying, screen printing, or dipping. The porous protective layer 110a also covers the gas inlet 111. However, since the porous protective layer 110a is a porous body, the measurement-object gas can flow through the porous protective layer 110a and reach the gas inlet 111. The thickness of the porous protective layer 110a is, for example, 100 μm to 700 μm, but is not particularly limited to this.

The protective cover 120 is disposed to surround the sensor element 110. The protective cover 120 includes an inner protective cover 130 having the shape of a cylinder with a bottom and configured to cover the front end of the sensor element 110, and the outer protective cover 140 having the shape of a cylinder with a bottom and configured to cover the inner protective cover 130. A first gas chamber 122 and a second gas chamber 126 are each formed as a space surrounded by the inner protective cover 130 and the outer protective cover 140, and the sensor element chamber 124 is formed as a space surrounded by the inner protective cover 130. The gas sensor 100, the sensor element 110, the inner protective cover 130, and the outer protective cover 140 share the same central axis. The protective cover 120 is made of metal (e.g., stainless steel).

The inner protective cover 130 includes a first member 131 and a second member 135. The first member 131 has a cylindrical large-diameter portion 132, the first cylindrical portion 134 cylindrical in shape and smaller in diameter than the large-diameter portion 132, and a step portion 133 connecting the large-diameter portion 132 to the first cylindrical portion 134. The first cylindrical portion 134 surrounds the sensor element 110. The second member 135 has the second cylindrical portion 136 larger in diameter than the first cylindrical portion 134, the end portion 138 having the shape of an inverted truncated cone and located downstream of the second cylindrical portion 136 in the front direction of the sensor element 110 (i.e., located below the second cylindrical portion 136 in FIG. 3), and a connecting portion 137 connecting the second cylindrical portion 136 to the end portion 138. The end portion 138 has a circular element-chamber outlet 138a (also referred to as an inner gas hole) in the center of the bottom surface thereof. The element-chamber outlet 138a communicates with the sensor element chamber 124 and the second gas chamber 126, and serves as an exit for the measurement-object gas from the sensor element chamber 124. The diameter of the element-chamber outlet 138a is, for example, 0.5 mm to 2.6 mm, but is not particularly limited to this. The element-chamber outlet 138a is located downstream of the gas inlet 111 in the front direction of the sensor element 110 (i.e., located below the gas inlet 111 in FIG. 3). In other words, the element-chamber outlet 138a is located farther from the back end of the sensor element 110 (i.e., from the upper end (not shown) of the sensor element 110 in FIG. 3) than the gas inlet 111 is (i.e., located below the gas inlet 111 in FIG. 3).

The large-diameter portion 132, the first cylindrical portion 134, the second cylindrical portion 136, and the end portion 138 share the same central axis. The large-diameter portion 132 is in contact with the housing 102 on the inner periphery thereof, and this secures the first member 131 to the housing 102. The second member 135 is in contact, on the outer periphery of the connecting portion 137 thereof, with the inner periphery of the outer protective cover 140, and is secured thereto by welding or the like. Alternatively, the second member 135 may be secured by making the outside diameter of the end portion 138 slightly larger than the inside diameter of a front end portion 146 of the outer protective cover 140 and press-fitting the end portion 138 into the front end portion 146.

The inner periphery of the second cylindrical portion 136 has a plurality of protrusions 136a protruding toward, and in contact with, the outer periphery of the first cylindrical portion 134. As illustrated in FIG. 4, three protrusions 136a are evenly spaced along the circumferential direction of the inner periphery of the second cylindrical portion 136. The protrusions 136a are substantially semispherical in shape. With the protrusions 136a, it becomes easier to secure the positional relation between the first cylindrical portion 134 and the second cylindrical portion 136. The protrusions 136a preferably press the outer periphery of the first cylindrical portion 134 inward in the radial direction. This allows the positional relation between the first cylindrical portion 134 and the second cylindrical portion 136 to be more reliably secured by the protrusions 136a. Note that the number of the protrusions 136a is not limited to three, and may be two or more than four. To stably secure the first cylindrical portion 134 and the second cylindrical portion 136 in place, it is preferable that there be three or more protrusions 136a.

The inner protective cover 130 has the element-chamber inlet 127 (see FIGS. 3, 4, and 7) which serves as an entrance for the measurement-object gas to the sensor element chamber 124. The element-chamber inlet 127 includes a cylindrical gap (gas flow passage) between the outer periphery of the first cylindrical portion 134 and the inner periphery of the second cylindrical portion 136. The element-chamber inlet 127 has a first outside opening 128a adjacent to the first gas chamber 122 which is a space having a plurality of outer inlets 144a disposed therein, a plurality of second outside openings 128b also adjacent to the first gas chamber 122, and an element-side opening 129 adjacent to the sensor element chamber 124 which is a space having the gas inlet 111 disposed therein.

The first outside opening 128a is an opening at an end portion (or upper end portion in FIGS. 3 and 7) of the cylindrical gap between the first cylindrical portion 134 and the second cylindrical portion 136, and the end portion is adjacent to the first gas chamber 122. The first outside opening 128a is formed closer to the back end of the sensor element 110 (i.e., to the upper end (not shown) of the sensor element 110 in FIG. 3) than the element-side opening 129 is. In other words, the element-side opening 129 is located downstream of the first outside opening 128a in the front direction. Accordingly, in the path of the measurement-object gas from any of the outer inlets 144a to the gas inlet 111, a flow passage extending through the first outside opening 128a toward the element-side opening 129 of the element-chamber inlet 127 is a flow passage from the back side (or upper side in FIG. 3) toward the front side (or lower side in FIG. 3) of the sensor element 110. Also, the flow passage extending through the first outside opening 128a toward the element-side opening 129 is a flow passage parallel to the back-front direction of the sensor element 110 (i.e., a flow passage in the up-down direction in FIG. 3).

The second outside openings 128b are a plurality of (six in the present embodiment) horizontal holes evenly spaced along the circumferential direction of the second cylindrical portion 136 (see FIG. 4). The second outside openings 128b are disposed in the second cylindrical portion 136, and pass through the second cylindrical portion 136 from the outer periphery to the inner periphery of the second cylindrical portion 136. The second outside openings 128b are holes formed in the shape of a circle (perfect circle). The diameter of each of the second outside openings 128b is, for example, 1 mm to 2 mm, but is not particularly limited to this. Note that all the second outside openings 128b have the same diameter in the present embodiment. The total cross-sectional area of the second outside openings 128b is, for example, 1 $mm^2$ to 4 $mm^2$. The cross-sectional area of each of the second outside openings 128b is an area in the direction perpendicular to the direction of the measurement-object gas passing through the second outside opening 128b (i.e., the direction from the outer periphery of the second cylindrical portion 136 toward the central axis in the present embodiment). The second outside openings 128b each allow the path of the measurement-object gas from the first outside opening 128a to the element-side opening 129 of the element-chamber inlet 127 (i.e., the cylindrical gap) to communicate in the middle thereof with the first gas chamber 122. Accordingly, the measurement-object gas flowing through the first outside opening 128a into the element-chamber inlet 127 joins the measurement-object gas flowing through the second outside opening 128b into the element-chamber inlet 127 and flows out through the element-side opening 129. The second outside openings 128b are formed closer to the back end of the sensor element 110 than the element-side opening 129 is. Accordingly, in the path of the measurement-object gas from any of the outer inlets 144a to the gas inlet 111, a flow passage extending through the second outside opening 128b toward the element-side opening 129 of the element-chamber inlet 127 is a flow passage from the back side (or upper side in FIG. 3) toward the front side (or lower side in FIG. 3) of the sensor element 110. The second outside openings 128b are located closer to the outer inlets 144a than the first outside opening 128a is. That is, the shortest distance between the outer inlet 144a (vertical hole 144c here), which is closest of all the outer inlets 144a to one of the second outside openings 128b, and the second outside opening 128b is smaller than the shortest distance between the outer inlet 144a (vertical hole 144c here), which is closest of all the outer inlets 144a to the first outside opening 128a, and the first outside opening 128a.

The element-side opening 129 is preferably formed at a distance A1 (see FIG. 7) of −1.5 mm or more from the gas inlet 111. The distance A1 may be greater than or equal to 0 mm, or may exceed 1.5 mm. Note that the distance A1 is a distance in the back-front direction (or up-down direction in FIG. 3) of the sensor element 110, and the direction from the front end toward the back end (i.e., the upward direction in FIG. 3) is defined to be positive. In the back-front direction of the sensor element 110, the distance A1 is a distance between an end portion of the opening of the gas inlet 111 closest to the element-side opening 129 and an end portion of the element-side opening 129 closest to the gas inlet 111. If, in FIG. 3, the gas inlet is a horizontal hole that opens in the side face of the sensor element 110 and the element-side opening 129 is located between the upper and lower ends of the opening of the gas inlet, then the distance A1 has a value of 0 mm. The upper limit of the distance A1 is determined by the shapes of the inner protective cover 130 and the sensor element chamber 124. The distance A1 may be 7.5 mm or less, 5 mm or less, or 2 mm or less, but is not particularly limited to this.

The element-side opening 129 is formed at a distance A2 (see FIG. 7) from the sensor element 110. The distance A2 is a distance in a direction perpendicular to the back-front direction of the sensor element 110. In the direction perpendicular to the back-front direction of the sensor element 110, the distance A2 is a distance between a portion of the sensor element 110 closest to the element-side opening 129 and an end portion of the element-side opening 129 closest to the sensor element 110. Increasing the distance A2 makes the sensor element 110 and the element-side opening 129 more distant from each other, and thus improves the effect of reducing the cooling of the sensor element 110. The distance A2 is, for example, 0.6 mm to 3.0 mm, but is not particularly limited to this. The element-side opening 129 opens in the direction from the back end toward the front end of the sensor element 110, and parallel to the back-front direction of the sensor element 110. That is, the element-side opening 129 opens in the downward direction (directly downward) in FIGS. 3 and 7. Therefore, the sensor element 110 is disposed at a position other than a region defined by imaginarily extending the element-chamber inlet 127 from the element-side opening 129 (i.e., other than a region directly below the element-side opening 129 in FIGS. 3 and 7). This can prevent the measurement-object gas flowing out of the element-side opening 129 from directly hitting the surface of the sensor element 110, and can reduce cooling of the sensor element 110.

The first outside opening 128a is formed at a distance A3 (see FIG. 7) from the outer inlet 144a. Note that the distance A3 is a distance in the back-front direction (or up-down direction in FIGS. 3 and 7) of the sensor element 110, and the direction from the front end toward the back end is defined to be positive, as in the case of the distance A1. In the back-front direction of the sensor element 110, the distance A3 is a distance between an end portion of the opening of the outer inlet 144a closest to the first outside opening 128a and an end portion of the first outside opening 128a closest to the outer inlet 144a. In the present embodiment, where the vertical hole 144c is formed as the outer inlet 144a, an upper end of the vertical hole 144c (i.e., an opening plane of the vertical hole 144c adjacent to the first gas chamber 122) is closest to the first outside opening 128a in the up-down direction in FIG. 3. Therefore, as illustrated in FIG. 7, the distance between the upper end of the vertical hole 144c and the first outside opening 128a is defined as the distance A3. The first outside opening 128a may be formed such that the distance A3 has a value greater than or equal to 0 or a positive value, or may be formed such that the distance A3 has a value less than or equal to 0 or a negative value. For example, the distance A3 has a negative value if the outer inlets 144a include a horizontal hole disposed in a side portion 143a to be higher than the first outside opening 128a in the up-down direction in FIG. 3 and then the distance between this horizontal hole and the first outside opening 128a in the up-down direction is smaller than the distance between the vertical hole 144c and the first outside opening 128a in the up-down direction. It is preferable, however, that the distance A3 have a value greater than or equal to 0. In other words, it is preferable that the first outside opening 128a be closer to the back end of the sensor element 110 (i.e., to the upper end (not shown) of the sensor element 110 in FIG. 3) than at least one of the outer inlets 144a is. In the present embodiment, it is preferable that the first outside opening 128a be located at the same level as, or above, the upper end of the vertical hole 144c. It is more preferable that the distance A3 be 3 mm or more.

The second outside opening 128b is formed at a distance A6 (see FIG. 7) from the outer inlet 144a. Like the distance A3, the distance A6 is a distance in the back-front direction (or up-down direction in FIGS. 3 and 7) of the sensor element 110, and the direction from the front end toward the back end is defined to be positive. Note that the distance A6 shares the same definition as the distance A3 except that the distance A6 is a distance to the second outside opening 128b. Accordingly, in the present embodiment, as illustrated in FIG. 7, the distance between the upper end of the vertical hole 144c and the second outside opening 128b is the distance A6. The second outside opening 128b may be formed such that the distance A6 has a value greater than or equal to 0 or a positive value, or may be formed such that the distance A6 has a value less than or equal to 0 or a negative value. The distance A6 is, for example, −3 mm to 3 mm, but is not particularly limited to this. The distance A6 may be −2 mm or more, −1 mm or more, 2 mm or less, or 1 mm or less. The position of the second outside opening 128b may be determined such that the distance A6 is smaller in absolute value than the distance A3. In the present embodiment, where the second outside openings 128b are located downstream of the first outside opening 128a in the front direction, the distance A6 is smaller in absolute value than the distance A3.

The outer periphery of the first cylindrical portion 134 and the inner periphery of the second cylindrical portion 136 are separated, at the element-side opening 129, by a distance A4 in the radial direction of the cylinder, and are separated, at the first outside opening 128a, by a distance A5 in the radial direction of the cylinder. Also, the outer periphery of the first cylindrical portion 134 and the inner periphery of the second cylindrical portion 136 are separated by a distance A7 at a portion (in the cross section illustrated in FIG. 4) where the protrusions 136a is in contact with the first cylindrical portion 134. The distance A4, the distance A5, and the distance A7 are each, for example, 0.3 mm to 2.4 mm, but are not particularly limited to this. Adjusting the values of the distance A4 and distance A5 makes it possible to adjust the opening area of the element-side opening 129 and the opening area of the first outside opening 128a. In the present embodiment, the distance A4, the distance A5, and the distance A7 are the same, and the opening area of the element-side opening 129 and the opening area of the first outside opening 128a are the same. In the present embodiment, the distance A4 (distance A5, distance A7) is equal to half the difference between the outside diameter of the first cylindrical portion 134 and the inside diameter of the second cylindrical portion 136. The distance between the element-side opening 129 and the first outside opening 128a in the up-down direction, that is, a length L1 of the element-chamber inlet 127 in the up-down direction is, for example, greater than 0 mm and less than or equal to 6.6 mm, but is not particularly limited to this. The distance between the element-side opening 129 and the second outside opening 128b, that is, a length L2 of the element-chamber inlet 127 in the up-down direction is, for example, greater than 0 mm and less than or equal to 5 mm, but is not particularly limited to this. The length L2 may be 3 mm or less, or may be 1 mm or less.

As illustrated in FIG. 3, the outer protective cover 140 has a cylindrical large-diameter portion 142, a cylindrical barrel part 143 connected to the large-diameter portion 142 and smaller in diameter than the large-diameter portion 142, and a front end portion 146 having the shape of a cylinder with a bottom and smaller in inside diameter than the barrel part 143. The barrel part 143 has the side portion 143a having a side face extending along the direction of the central axis of the outer protective cover 140 (i.e., along the up-down direction in FIG. 3), and a step portion 143b serving as a bottom portion of the barrel part 143 and connecting the side portion 143a to the front end portion 146. Note that the large-diameter portion 142, the barrel part 143, and the front end portion 146 share the same central axis as the inner protective cover 130. The large-diameter portion 142 is in contact with the housing 102 and the large-diameter portion 132 on the inner periphery thereof, and this secures the outer protective cover 140 to the housing 102. The barrel part 143 is disposed to cover the outer peripheries of the first cylindrical portion 134 and second cylindrical portion 136. The front end portion 146 is disposed to cover the end portion 138, and is in contact with the outer periphery of the connecting portion 137 on the inner periphery thereof. The front end portion 146 has a side face extending along the direction of the central axis of the outer protective cover 140 (i.e., along the up-down direction in FIG. 3), and has a side portion 146a whose outside diameter is smaller than the inside diameter of the side portion 143a and a bottom portion 146b which is the bottom of the outer protective cover 140. The front end portion 146 is located downstream of the barrel part 143 in the front direction. The outer protective cover 140 has the plurality of (six in the present embodiment) outer inlets 144a formed in the barrel part 143 and each serving as an entrance for the measurement-object gas from the outside, and a plurality of (six in the present embodiment) outer outlets 147a formed in the front end portion 146 and each serving as an exit for the measurement-object gas to the outside.

The outer inlets 144a are holes (also referred to as first outer gas holes) that communicate with the outside (exterior) of the outer protective cover 140 and with the first gas chamber 122. The outer inlets 144a include a plurality of (six in the present embodiment) vertical holes 144c formed at regular intervals in the step portion 143b (see FIGS. 3 to 6). The side portion of the outer protective cover 140 (i.e., the side portion 143a of the barrel part 143 here) does not have the outer inlets 144a. The outer inlets 144a (vertical holes 144c) are holes formed in the shape of a circle (perfect circle). The diameters of the six outer inlets 144a are, for example, 0.5 mm to 2.0 mm, but are not particularly limited to this. The diameters of the outer inlets 144a may be 1.5 mm or less. Note that all the vertical holes 144c have the same diameter in the present embodiment.

Figure 8:
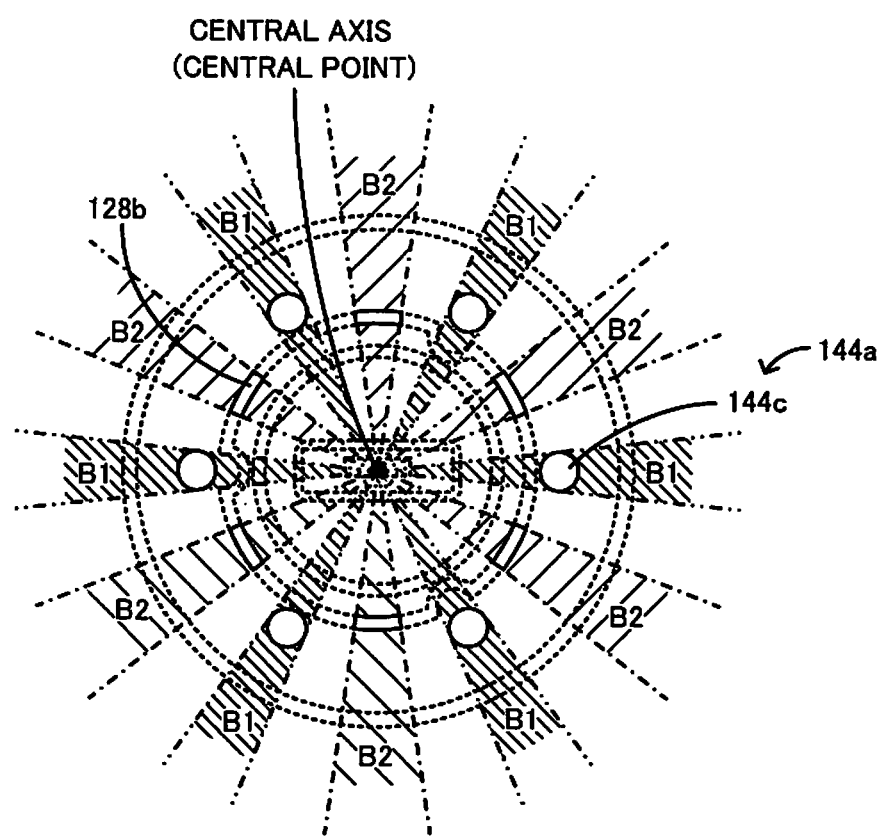
FIG. 8 is a diagram illustrating existence regions B1 of vertical holes 144c and existence regions B2 of second outside openings 128b.

The vertical holes 144c of the outer inlets 144a and the second outside openings 128b are preferably arranged to be displaced in the circumferential direction of the outer protective cover 140. This will be described with reference to FIG. 8. FIG. 8 is a diagram illustrating existence regions B1 of the vertical holes 144c and existence regions B2 of the second outside openings 128b. The diagram of FIG. 8 is obtained by projecting the vertical holes 144c, the second outside openings 128b, and the central axis of the outer protective cover 140 onto a plane perpendicular to the central axis (e.g., onto a plane same as that in FIG. 4) along the axial direction of the outer protective cover 140. In the projected plane (e.g., FIG. 8), as viewed in the radial direction of the outer protective cover 140 from the projected central axis (hereinafter also referred to as a central point), regions where there are the projected vertical holes 144c are defined as the existence regions B1 and regions there are the projected second outside openings 128b are defined as the existence regions B2. The existence regions B1 and B2 are hatched in FIG. 8. As illustrated in FIG. 8, each existence region B1 is a region including one vertical hole 144c and defined by lines that extend from the central point and are tangent to the vertical hole 144c on both sides of the vertical hole 144c. The number of the existence regions B1 is six, which is the same as that of the vertical holes 144c. The same applies to the existence regions B2. That is, like the second outside openings 128b, there are six existence regions B2. As described above, the vertical holes 144c and the second outside openings 128b are preferably arranged to be displaced in the circumferential direction of the outer protective cover 140. That is, the existence regions B1 and the existence regions B2 defined as described above preferably do not overlap. In the present embodiment, as illustrated in FIG. 8, the vertical holes 144c and the second outside openings 128b are arranged such that the existence regions B1 and the existence regions B2 do not overlap. Additionally, in the present embodiment, the vertical holes 144c of the outer inlets 144a and the second outside openings 128b are formed to be alternately and evenly spaced along the circumferential direction of the inner protective cover 130 and the outer protective cover 140, as illustrated in FIGS. 4 and 8. That is, in FIGS. 4 and 8, an angle formed by a line connecting the center of each vertical hole 144c with the central axis of the inner protective cover 130 and the outer protective cover 140 and a line connecting the center of one second outside opening 128b adjacent to the vertical hole 144c with the central axis of the inner protective cover 130 and the outer protective cover 140 is 30° (360°/12). Even when the vertical holes 144c and the second outside openings 128b are not alternately and evenly spaced, it is still possible to arrange the vertical holes 144c and the second outside openings 128b such that the existence regions B1 and the existence regions B2 do not overlap. Note that "the existence regions B1 and the existence regions B2 do not overlap" refers not only to the case where the existence regions B1 and the existence regions B2 are spaced apart in the circumferential direction of the outer protective cover 140 as illustrated in FIG. 8, but also to the case where the existence regions B1 and the existence regions B2 are in contact in the circumferential direction.

The second outside openings 128*b* preferably do not open toward regions extending from the outer inlets 144*a*. The regions extending from the outer inlets 144*a* are regions reached by directional light imaginarily applied in the direction along the central axis of the outer inlets 144*a*. That is, when the second outside openings 128*b* do not open toward the regions extending from the outer inlets 144*a*, the light does not reach the inside of each second outside opening 128*b*. In the present embodiment, the regions extending from the outer inlets 144*a* are regions directly above the vertical holes 144*c*. As can be seen in FIGS. 3 and 7, the second outside openings 128*b* of the present embodiment do not open toward the regions extending from the outer inlets 144*a*.

The outer outlets 147*a* are holes (also referred to as second outer gas holes) that communicate with the outside (exterior) of the outer protective cover 140 and with the second gas chamber 126. The outer outlets 147*a* include a plurality of (six in the present embodiment) vertical holes 147*c* formed in the bottom portion 146*b* of the front end portion 146 at regular intervals along the circumferential direction of the outer protective cover 140 (see FIGS. 3, 5, and 6). The side portion of the outer protective cover 140 (i.e., the side portion 146*a* of the front end portion 146 here) does not have the outer outlets 147*a*. The outer outlets 147*a* (vertical holes 147*c*) are holes formed in the shape of a circle (perfect circle). The diameters of the six outer outlets 147*a* are, for example, 0.5 mm to 2.0 mm, but are not particularly limited to this. The diameters of the outer outlets 147*a* may be 1.5 mm or less. Note that all the outer outlets 147*a* have the same diameter in the present embodiment.

The outer protective cover 140 and the inner protective cover 130 form the first gas chamber 122 as a space between the barrel part 143 and the inner protective cover 130. More specifically, the first gas chamber 122 is a space surrounded by the step portion 133, the first cylindrical portion 134, the second cylindrical portion 136, the large-diameter portion 142, the side portion 143*a*, and the step portion 143*b*. The sensor element chamber 124 is a space surrounded by the inner protective cover 130. The outer protective cover 140 and the inner protective cover 130 form the second gas chamber 126 as a space between the front end portion 146 and the inner protective cover 130. More specifically, the second gas chamber 126 is a space between the end portion 138 and the front end portion 146. Note that the first gas chamber 122 and the second gas chamber 126 do not directly communicate with each other, as the inner periphery of the front end portion 146 is in contact with the outer periphery of the connecting portion 137.

A description will now be given of how the measurement-object gas flows inside the protective cover 120 when the gas sensor 100 detects the concentration of a predetermined gas. The measurement-object gas in the pipe 20 first flows through at least one of the plurality of outer inlets 144*a* (vertical holes 144*c*) into the first gas chamber 122. Next, from the first gas chamber 122, the measurement-object gas flows through at least one of the first outside opening 128*a* and the second outside openings 128*b* into the element-chamber inlet 127. The measurement-object gas then flows out of the element-chamber inlet 127 through the element-side opening 129, and flows into the sensor element chamber 124. At least part of the measurement-object gas flowing through the element-side opening 129 into the sensor element chamber 124 reaches the gas inlet 111 of the sensor element 110. When the measurement-object gas reaches the gas inlet 111 and flows into the sensor element 110, the sensor element 110 generates an electrical signal (voltage or current) in accordance with the concentration of the predetermined gas (e.g., NOx or $O_2$) in the measurement-object gas. The gas concentration is detected on the basis of the electrical signal. The measurement-object gas in the sensor element chamber 124 flows through the element-chamber outlet 138*a* into the second gas chamber 126, and then flows through at least one of the plurality of outer outlets 147*a* to the outside. For example, a controller (not shown) controls the output of the heater in the sensor element 110 to maintain a predetermined temperature.

The element-chamber inlet 127 has the first outside opening 128*a* and the second outside openings 128*b* as described above. Accordingly, flow passages along which the measurement-object gas flowing in through at least one of the outer inlets 144*a* passes through the element-chamber inlet 127 include a flow passage (also referred to as a first flow passage) extending through the first outside opening 128*a* to the element-side opening 129, and a flow passage (also referred to as a second flow passage) extending through at least one of the second outside openings 128*b* to the element-side opening 129. As described above, the second outside openings 128*b* are located closer to the outer inlets 144*a* than the first outside opening 128*a* is, and the second outside openings 128*b* are arranged such that there is a path that is shorter than the shortest path of the measurement-object gas extending from the outer inlet 144*a* through the first outside opening 128*a* to the gas inlet 111. In other words, the length of the shortest path of the measurement-object gas extending from the outer inlet 144*a* through the second outside opening 128*b* to the gas inlet 111 (also referred to as a shortest second path length P2) is shorter than the length of the shortest path of the measurement-object gas extending from the outer inlet 144*a* through the first outside opening 128*a* to the gas inlet 111 (also referred to as a shortest first path length P1). The shortest first and second path lengths P1 and P2 are each the length of the shortest path of the flow passage of the measurement-object gas from the outside opening plane of the outer inlet 144*a* to the outside opening plane of the gas inlet 111. When there are a plurality of outer inlets 144*a*, the shortest of the shortest path lengths from the respective outer inlets 144*a* to the gas inlet 111 is defined as the shortest first path length P1. The same applies to the shortest second path length P2.

Figure 9:
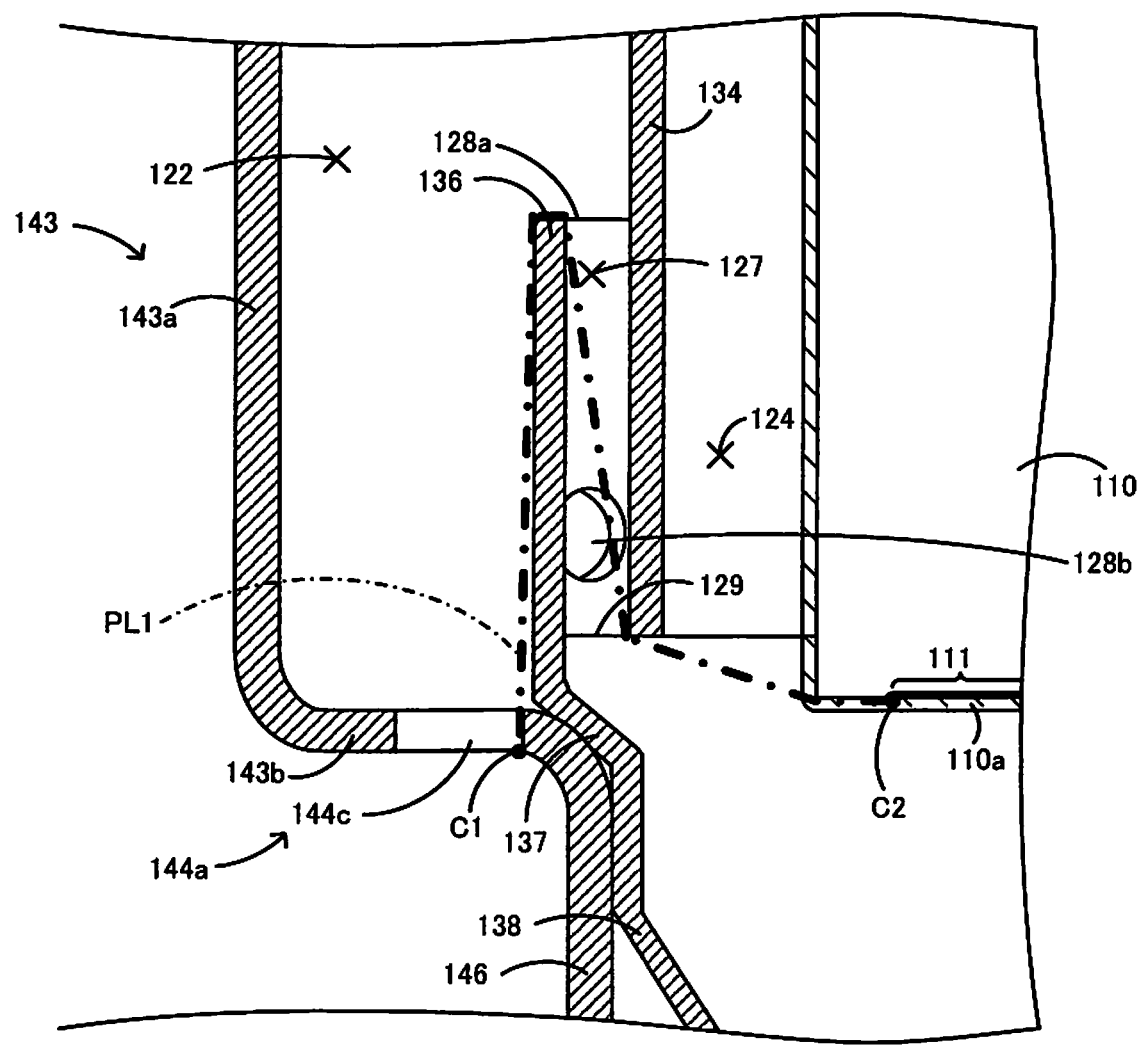
FIG. 9 is an enlarged view of part of an E-E cross section of FIG. 4 along the path of a shortest first path length P1.

The shortest first path length P1 according to the present embodiment will now be described in detail. In the present embodiment, the outer protective cover 140 has the vertical holes 144*c* as the outer inlets 144*a*. Also in the present embodiment, as illustrated in FIG. 4, the opening plane of the gas inlet 111 is rectangular in shape and is displaced upward in FIG. 4 from the central axis of the inner protective cover 130 and the outer protective cover 140. From the points described above and the positional relation of the vertical holes 144*c*, the gas inlet 111, and the first outside opening 128*a*, the length of the shortest path extending from the upper left one of the six vertical holes 144*c* in FIG. 4 through the first outside opening 128*a* to the gas inlet 111 is defined as the shortest first path length P1 of the protective cover 120 in the present embodiment. Note, in the present embodiment, that the length of the shortest path extending from the vertical hole 144*c* at the upper right position in FIG. 4 through the first outside opening 128*a* to the gas inlet 111 has the same value as above (=the shortest first path length P1). FIG. 9 is an enlarged view of part of an E-E cross section of FIG. 4 along the path of the shortest first path length P1. Note that the E-E cross section of FIG. 4 is a cross section passing through the vertical hole 144*c* at the upper left position in FIG. 4 and the upper left end of the gas inlet 111. Note also that the vertical hole 144c illustrated in FIG. 9 is the vertical hole 144c located at the upper left position in FIG. 4. As illustrated in FIG. 9, the length of the shortest path (polygonal line PL1) extending from an end portion C1 (right end in FIG. 9) of the outside opening plane of the vertical hole 144c closest to the first outside opening 128a, through the first outside opening 128a, to an end portion C2 (left end in FIG. 9) of the outside opening plane of the gas inlet 111 is the shortest first path length P1. Note that the shortest first path length P1 is defined without taking into account the presence of the porous protective layer 110a. For example, in FIG. 9, a part of the path represented by the polygonal line PL1, extending from the element-side opening 129 to the gas inlet 111, is defined as a path represented by a straight line connecting the element-side opening 129 to the lower left end portion of the sensor element 110 and a straight line connecting the lower left end portion of the sensor element 110 to the left end of the opening plane of the gas inlet 111, without taking into account the presence of the porous protective layer 110a.

Figure 10:
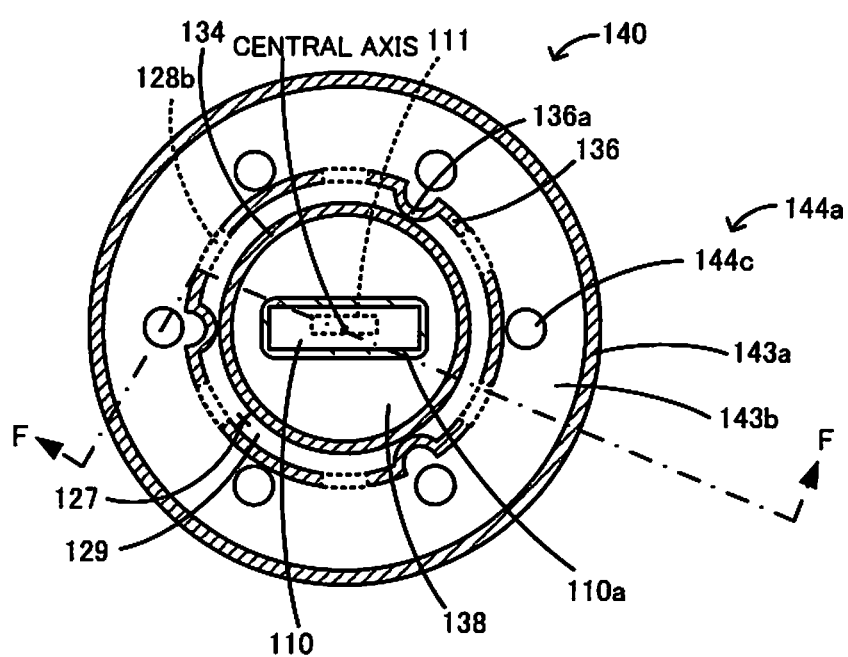
FIG. 10 is a cross-sectional view showing the location of an F-F cross section along the path of a shortest second path length P2.
Figure 11:
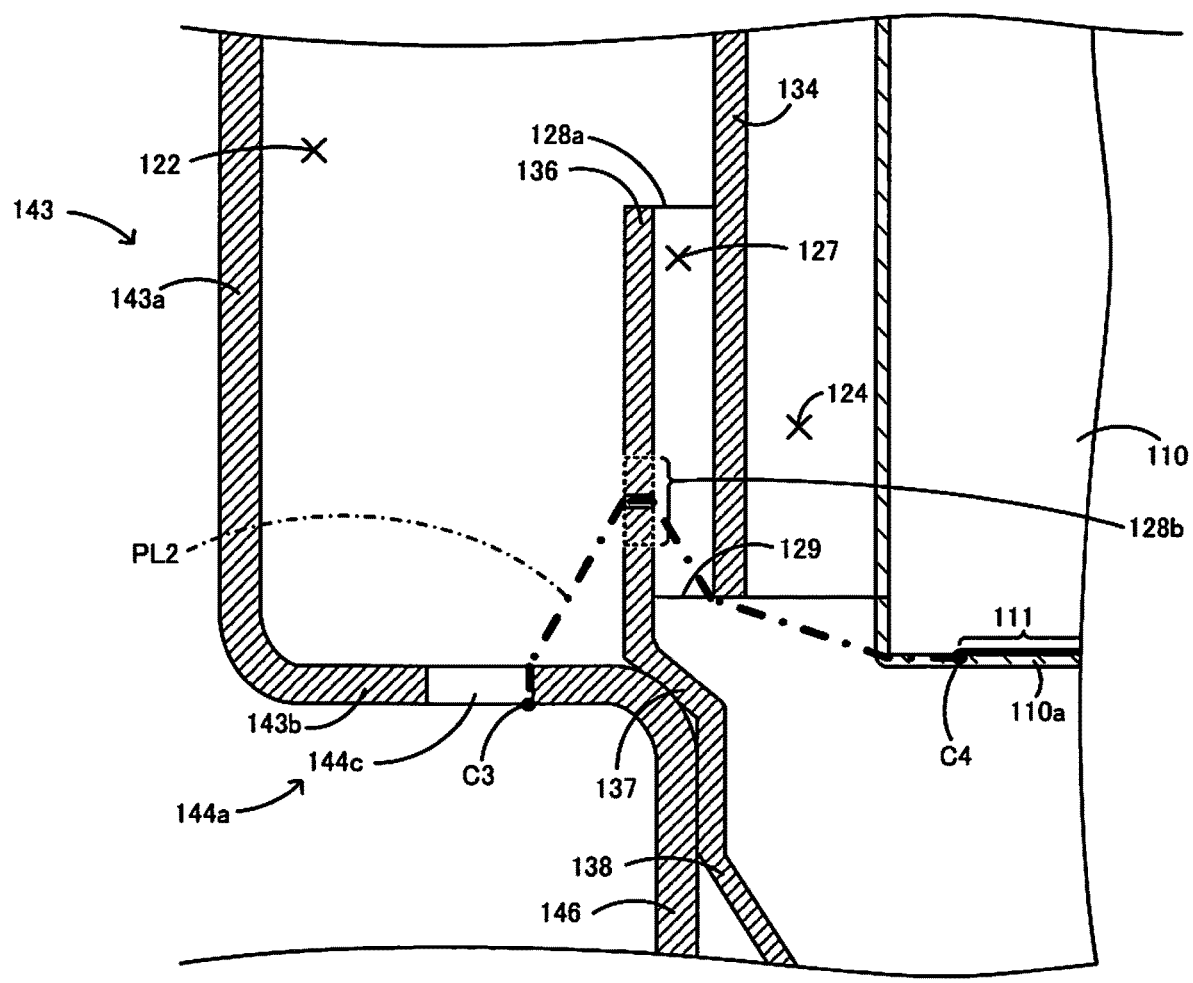
FIG. 11 is an enlarged view of part of the F-F cross section of FIG. 10.

The shortest second path length P2 according to the present embodiment will now be described in detail. FIG. 10 is a cross-sectional view showing the location of an F-F cross section along the path of the shortest second path length P2. FIG. 11 is an enlarged view of part of the F-F cross section of FIG. 10. Note that FIG. 10 shows the location of the F-F cross section in the same cross-sectional view as FIG. 4. Note also that the vertical hole 144c illustrated in FIG. 11 is the vertical hole 144c located at the leftmost position in FIG. 10. From the positional relation of the outer inlets 144a (vertical holes 144c here), the gas inlet 111, and the second outside openings 128b, the length of the shortest path extending from the leftmost one of the six vertical holes 144c in FIG. 10 through the upper left one of the second outside openings 128b in FIG. 10 to the gas inlet 111 is defined as the shortest second path length P2 of the protective cover 120 in the present embodiment. Note, in the present embodiment, that the length of the shortest path extending from the vertical hole 144c at the rightmost position in FIG. 10 through the second outside opening 128b at the upper right position in FIG. 10 to the gas inlet 111 has the same value as above (=the shortest second path length P2). As illustrated in FIG. 11, the length of the shortest path (polygonal line PL2) extending from an end portion C3 (right end in FIG. 11) of the outside opening plane of the vertical hole 144c closest to the second outside opening 128b, through the second outside opening 128b, to an end portion C4 (left end in FIG. 11) of the outside opening plane of the gas inlet 111 is the shortest second path length P2. Note that, like the shortest first path length P1, the shortest second path length P2 is defined without taking into account the presence of the porous protective layer 110a.

As described above, there are the second outside openings 128b arranged such that the shortest second path length P2 is smaller than the shortest first path length P1. Therefore, even when the measurement-object gas flows at low velocity (e.g., 4 m/s or less), the measurement-object gas flowing in through at least one of the outer inlets 144a can pass through the second outside opening 128b (i.e., through the second flow passage) and reach the gas inlet 111 in a relatively short time. Thus, for example, as compared to the case where there are no second outside openings 128b, the loss of responsiveness of the sensor element 110 when the measurement-object gas flows at low velocity can be reduced. When the measurement-object gas flows at high velocity or rate, since there is the first flow passage extending through the first outside opening 128a as well as the second flow passage extending through the second outside opening 128b, the flow velocity or rate of the measurement-object gas passing through the element-chamber inlet 127 is not easily reduced. Therefore, in the gas sensor 100 according to the present embodiment, for example, as compared to the case where there is no first outside opening 128a, the loss of responsiveness when the measurement-object gas flows at high velocity can be reduced. In the case of absence of the first outside opening 128a, for example, the diameter of the second outside openings 128b may be increased to reduce the loss of responsiveness at high flow velocity. In this case, however, if the diameter of the second outside openings 128b is too large, water may pass through the second outside openings 128b to reach the sensor element 110, and this may degrade the heat retaining properties of the sensor element 110. In the gas sensor 100 according to the present embodiment, which has both the first outside opening 128a and the second outside openings 128b, it is possible to reduce not only the degradation of heat retaining properties, but also the loss of responsiveness when the measurement-object gas flows at high velocity.

The shortest second path length P2 is preferably, for example, 5.0 mm to 11.0 mm. If the shortest second path length P2 is 11.0 mm or less, the effect of reducing the loss of responsiveness at low flow velocity can be more reliably achieved. If the shortest second path length P2 is 5.0 mm or more, problems which may arise when the shortest second path length P2 is too small can be reduced. Examples of such problems are that external poisoning material or water flowing in through the outer inlet 144a easily reaches the sensor element 110, the sensor element 110 is easily cooled by the measurement-object gas, and the output of the heater required to prevent cooling of the sensor element 110 is increased. The shortest second path length P2 is preferably 10.5 mm or less, more preferably 10.0 mm or less, more preferably 9.5 mm or less, still more preferably 9.0 mm or less, and even more preferably 8.5 mm or less. The smaller the shortest second path length P2, the higher the effect of reducing the loss of responsiveness at low flow velocity. The shortest second path length P2 may be 6.0 mm or more. The shortest first path length P1 may be any length greater than the shortest second path length P2. For example, the shortest first path length P1 may be greater than 11.0 mm, greater than or equal to 13.0 mm, or smaller than or equal to 20.0 mm. The difference between the shortest first path length P1 and the shortest second path length P2 (P1−P2) may be 3 mm or more, 5 mm or more, or 6 mm or more. The difference (P1−P2) may be 10 mm or less.

In the present embodiment, from the shape and position of the gas inlet 111 described above, the length of the shortest path extending from each of the four vertical holes 144c, other than the rightmost and leftmost ones of the vertical holes 144c in FIG. 10, through the second outside opening 128b to the gas inlet 111 is slightly greater than the shortest second path length P2. When the length of the shortest path extending from each of the plurality of vertical holes 144c through the second outside opening 128b is different as described above, it is preferable that the shortest path lengths from a larger number of vertical holes 144c be in the 5.0 mm to 11.0 mm range. In the present embodiment, the shortest second path length P2 from not only each of the rightmost and leftmost ones of the vertical holes 144c in FIG. 10, but also the length of the shortest path extending from any of the vertical holes 144c through the second outside opening 128b is in the 5.0 mm to 11.0 mm range.

In the gas sensor 100 of the present embodiment described in detail above, the second outside openings 128b of the inner protective cover 130 are arranged such that the path of the measurement-object gas from the first outside opening 128a to the element-side opening 129 of the element-chamber inlet 127 communicates in the middle thereof with the first gas chamber 122, and that there is a path (i.e., the path of the shortest second path length P2) shorter than the shortest path (shortest first path length P1) of the measurement-object gas extending from the outer inlet 144a through the first outside opening 128a to the gas inlet 111. With the second outside openings 128b, the loss of responsiveness when the measurement-object gas flows at low velocity can be reduced. With the first outside opening 128a, the loss of responsiveness when the measurement-object gas flows at high velocity can also be reduced.

The second outside openings 128b do not open toward the regions extending from the outer inlets 144a. Therefore, even if water enters the interior of the outer protective cover 140 through the outer inlets 144a, the water does not easily flow in through the second outside openings 128b. It is thus possible to prevent water from easily adhering to the sensor element 110 and improve heat retaining properties of the sensor element 110.

The outer protective cover 140 includes the cylindrical barrel part 143 having the side portion 143a and the step portion 143b (bottom portion), and the outer inlets 144b include the vertical holes 144c disposed in the step portion 143b of the barrel part 143 of the outer protective cover 140. When the vertical holes 144c, the second outside openings 128b, and the central axis of the outer protective cover 140 are projected onto a plane perpendicular to the central axis, the projected vertical holes 144c and the projected second outside openings 128b do not overlap as viewed in the radial direction of the outer protective cover 140 from the projected central axis. That is, there are no existence regions B2 that overlap the existence regions B1 in FIG. 8. Accordingly, the vertical holes 144c included in the outer inlets 144a and the second outside openings 128b are relatively distant in the circumferential direction of the outer protective cover 140 and the inner protective cover 130. Even if water enters the interior of the outer protective cover 140 through the vertical holes 144c, the water does not easily flow in through the second outside openings 128b. It is thus possible to prevent water from easily adhering to the sensor element 110 and improve heat retaining properties of the sensor element 110. The second outside openings 128b are horizontal holes in the present embodiment. In this case, if the second outside openings 128b and the vertical holes 144c are located relatively close in the circumferential direction, the flow of the measurement-object gas passing through the vertical holes 144c may interfere with the flow of the measurement-object gas passing through the second outside openings 128b. This may increase the time before the measurement-object gas reaches the gas inlet 111, and may cause loss of responsiveness. When the vertical holes 144c and the second outside openings 128b are arranged such that there are no existence regions B2 overlapping the existence regions B1, it is possible to reduce such loss of responsiveness.

The outer protective cover 140 includes the cylindrical barrel part 143 having the side portion 143a and the step portion 143b (bottom portion), and the side portion 143a does not have the outer inlets 144a. If the side portion 143a of the barrel part 143 has the outer inlets 144a (e.g., horizontal holes), water may easily enter the interior of the outer protective cover 140 through the horizontal holes. When the side portion 143a does not have the outer inlets 144a, the amount of such water entry can be reduced. In the present embodiment, where the second outside openings 128b are horizontal holes, water tends to flow in more easily through the second outside openings 128b than through the first outside opening 128a that opens upward in FIG. 3. It is thus significant for the side portion 143a not to have the outer inlets 144a.

The inner protective cover 130 forms the element-chamber inlet 127 such that the element-side opening 129 opens in the front direction. This can prevent the measurement-object gas flowing out through the element-side opening 129 from perpendicularly hitting the surface (except the gas inlet 111) of the sensor element 110, and can also prevent the measurement-object gas from traveling a long distance over the surface of the sensor element 110 to reach the gas inlet 111. It is thus possible to reduce cooling of the sensor element 110. Additionally, since cooling of the sensor element 110 is reduced by adjusting the orientation of the element-side opening 129, not by reducing the flow rate or velocity of the measurement-object gas inside the inner protective cover 130, the loss of responsiveness in gas concentration detection can be reduced. It is thus possible to ensure both responsiveness and heat retaining properties of the sensor element 110.

It is obvious that the present invention is not at all limited to the embodiment described above, and can be implemented in various forms within the technical scope of the present invention.

For example, the shape of the protective cover 120 is not limited to the embodiment described above. The shape of the protective cover 120 and the shapes, numbers, and arrangements of the element-chamber inlet 127, the element-chamber outlet 138a, the outer inlets 144a, and the outer outlets 147a may be changed appropriately. For example, although the element-chamber inlet 127 includes a gap between the first member 131 and the second member 135, the configuration is not limited to this. The element-chamber inlet may be of any shape as long as it serves as an entrance to the sensor element chamber 124 and has the first outside opening 128a, the second outside openings 128b, and the element-side opening 129 which are formed such that the shortest second path length P2 is smaller than the shortest first path length P1. For example, the element-chamber inlet may be a through hole formed in the inner protective cover 130. Even when the element-chamber inlet is a through hole, the element-chamber inlet may form a flow passage extending from the back side toward the front side of the sensor element 110. For example, the element-chamber inlet may have a vertical hole or a hole that is inclined with respect to the up-down direction in FIG. 3. The element-side opening may open in the front direction. There may be more than one element-chamber inlet 127. The element-chamber outlet 138a, the outer inlets 144a, and the outer outlets 147a do not necessarily need to be holes, and may be gaps formed by a plurality of components of the protective cover 120. The number of each of the element-chamber outlet 138a, the outer inlets 144a, and the outer outlets 147a may be any number greater than or equal to one. Although the outer inlets 144a include the vertical holes 144c in the description above, the outer inlets 144a may include one or more of vertical holes, horizontal holes formed in the side portion 143a, and corner holes formed at the corner on the boundary between the side portion 143a and the step portion 143b. Similarly, the element-chamber inlet 127, the element-chamber outlet 138a, and the outer outlets 147a may also include one or more of horizontal holes, vertical holes, and corner holes. As described above, however, the outer inlets 144a preferably do not include any horizontal holes, that is, the side portion 143a preferably does not have the outer inlets 144a. If the outer inlets 144a include one or more of horizontal holes, vertical holes, and corner holes, the outer inlets 144a and the second outside openings 128b may be arranged such that when the outer inlets 144a, the second outside openings 128b, and the central axis of the outer protective cover 140 are projected onto a plane perpendicular to the central axis, the projected outer inlets 144a and the projected second outside openings 128b do not overlap as viewed in the radial direction of the outer protective cover 140 from the projected central axis.

Figure 12:
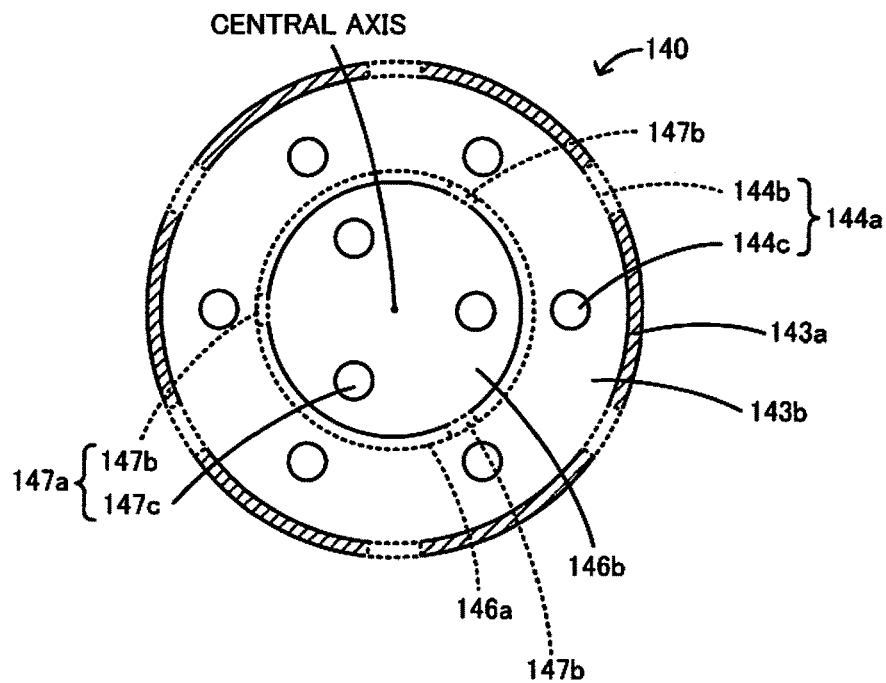
FIG. 12 is a cross-sectional view of the outer protective cover 140 having horizontal holes 144b and 147b.
Figure 13:
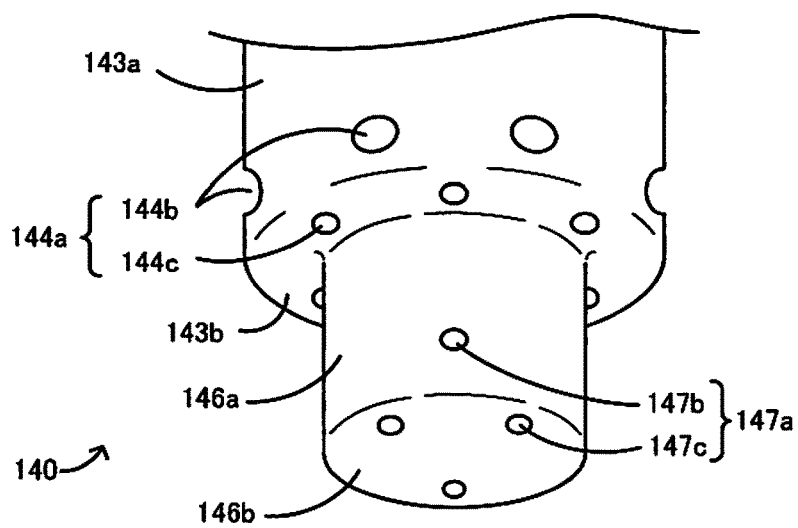
FIG. 13 is a perspective view of the outer protective cover 140 having the horizontal holes 144b and 147b.

An example of horizontal holes will be described. FIGS. 12 and 13 are a cross-sectional view and a perspective view, respectively, illustrating the outer inlets 144a including a plurality of (six here) horizontal holes 144b formed in the side portion 143a and the outer outlets 147a including a plurality of (three here) horizontal holes 147b formed in the side portion 146a. In the outer protective cover 140 illustrated in FIGS. 12 and 13, the outer inlets 144a include the six horizontal holes 144b and the six vertical holes 144c. The horizontal holes 144b and the vertical holes 144c are formed to be alternately and evenly spaced along the circumferential direction of the outer protective cover 140. The outer outlets 147a include the three horizontal holes 147b and three vertical holes 147c. The horizontal holes 147b and the vertical holes 147c are formed to be alternately and evenly spaced along the circumferential direction of the outer protective cover 140.

Figure 14:
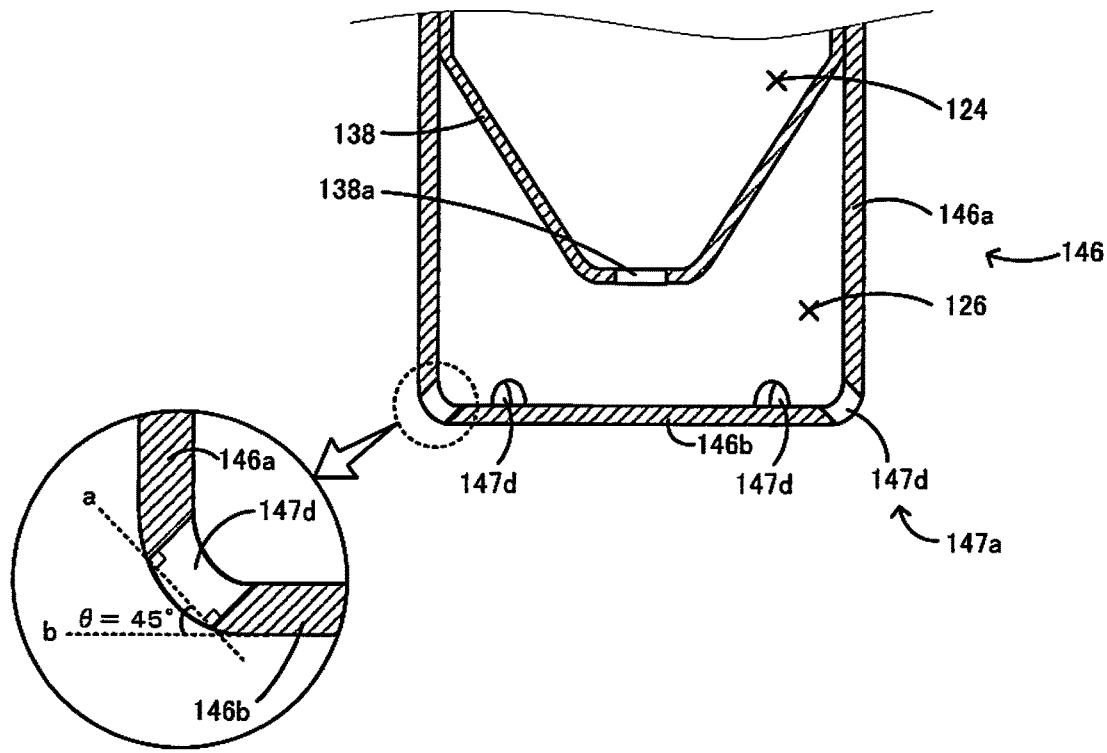
FIG. 14 is a cross-sectional view of outer outlets 147a including corner holes 147d.

An example of corner holes will be described. FIG. 14 is a cross-sectional view illustrating the outer outlets 147a including a plurality of corner holes 147d. As illustrated, the outer outlets 147a disposed in the front end portion 146 of FIG. 14 do not include the vertical holes 147c and include, instead, a plurality of corner holes 147d located at the corner on the boundary between the side portion 146a and the bottom portion 146b. Six corner holes 147d (only four of them are shown in FIG. 14) are evenly spaced along the circumferential direction of the outer protective cover 140. The corner holes 147d may be configured such that an angle θ formed by the outside opening plane of each corner hole 147d (indicated by straight line "a" in the enlarged view in the lower left part of FIG. 14) and the bottom surface (lower surface) of the bottom portion 146b (indicated by straight line "b" in the enlarged view in the lower left part of FIG. 14) is in the 10° to 80° range. The angle θ is 45° in FIG. 14. Even when corner holes are formed at the corner on the boundary between the side portion 143a and the step portion 143b in the embodiment described above, the angle θ formed by the outside opening plane of each corner hole and the bottom surface (lower surface) of the step portion 143b may be in the 10° to 80° range.

Although the inner periphery of the second cylindrical portion 136 has the protrusions 136a in the embodiment described above, the configuration is not limited to this. It is only necessary that at least one of the outer periphery of the first cylindrical portion 134 and the inner periphery of the second cylindrical portion 136 have a plurality of protrusions protruding to come into contact with the other periphery. In the embodiment described above, as illustrated in FIGS. 3 and 4, the outer periphery of the second cylindrical portion 136 is recessed inward at portions corresponding to the protrusions 136a. However, the configuration is not limited to this, and the outer periphery of the second cylindrical portion 136 does not necessarily need to be recessed. The protrusions 136a do not necessarily need to be semispherical, and may be of any shape. The outer periphery of the first cylindrical portion 134 and the inner periphery of the second cylindrical portion 136 do not necessarily need to have the protrusions 136a.

Figure 15:
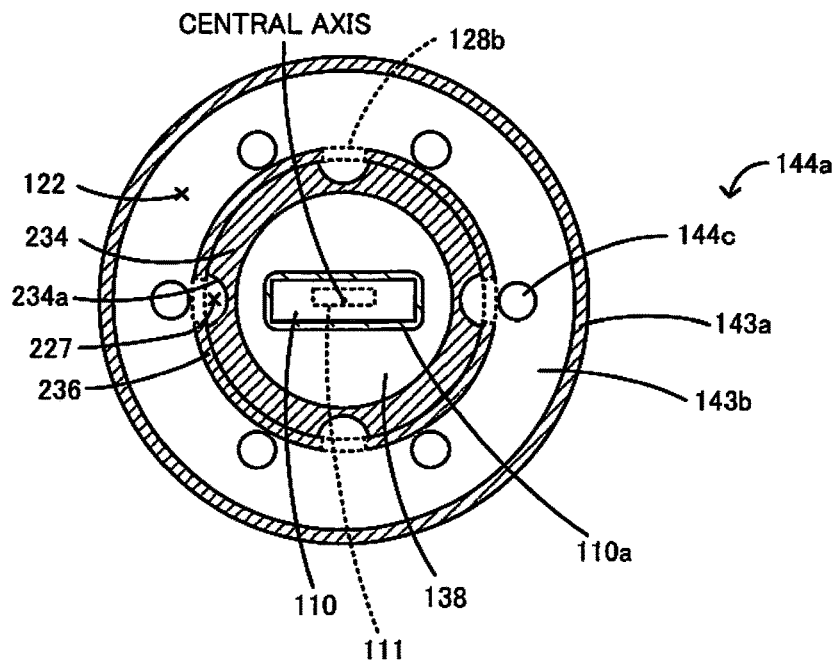
FIG. 15 is a cross-sectional view of an element-chamber inlet 227 according to a modification.

Although the element-chamber inlet 127 is a cylindrical gap between the outer periphery of the first cylindrical portion 134 and the inner periphery of the second cylindrical portion 136 in the embodiment described above, the configuration is not limited to this. For example, at least one of the outer periphery of the first cylindrical portion and the inner periphery of the second cylindrical portion may have recessed portions (grooves), and the element-chamber inlet may include gaps formed by the recessed portions between the first cylindrical portion and the second cylindrical portion. FIG. 15 is a cross-sectional view of an element-chamber inlet 227 according to a modification. As illustrated in FIG. 15, the outer periphery of a first cylindrical portion 234 is in contact with the inner periphery of a second cylindrical portion 236. The outer periphery of the first cylindrical portion 234 has a plurality of (four in FIG. 15) recessed portions 234a evenly spaced. The element-chamber inlet 227 includes gaps between the recessed portions 234a and the inner periphery of the second cylindrical portion 236. The upper ends of the gaps serve as the first outside opening 128a (not shown), and the lower ends of the gaps serve as the element-side opening 129 (not shown). The second outside openings 128b are horizontal holes formed in the second cylindrical portion 236 to allow the gaps between the recessed portions 234a and the inner periphery of the second cylindrical portion 236 to communicate with the first gas chamber 122.

Figure 16:
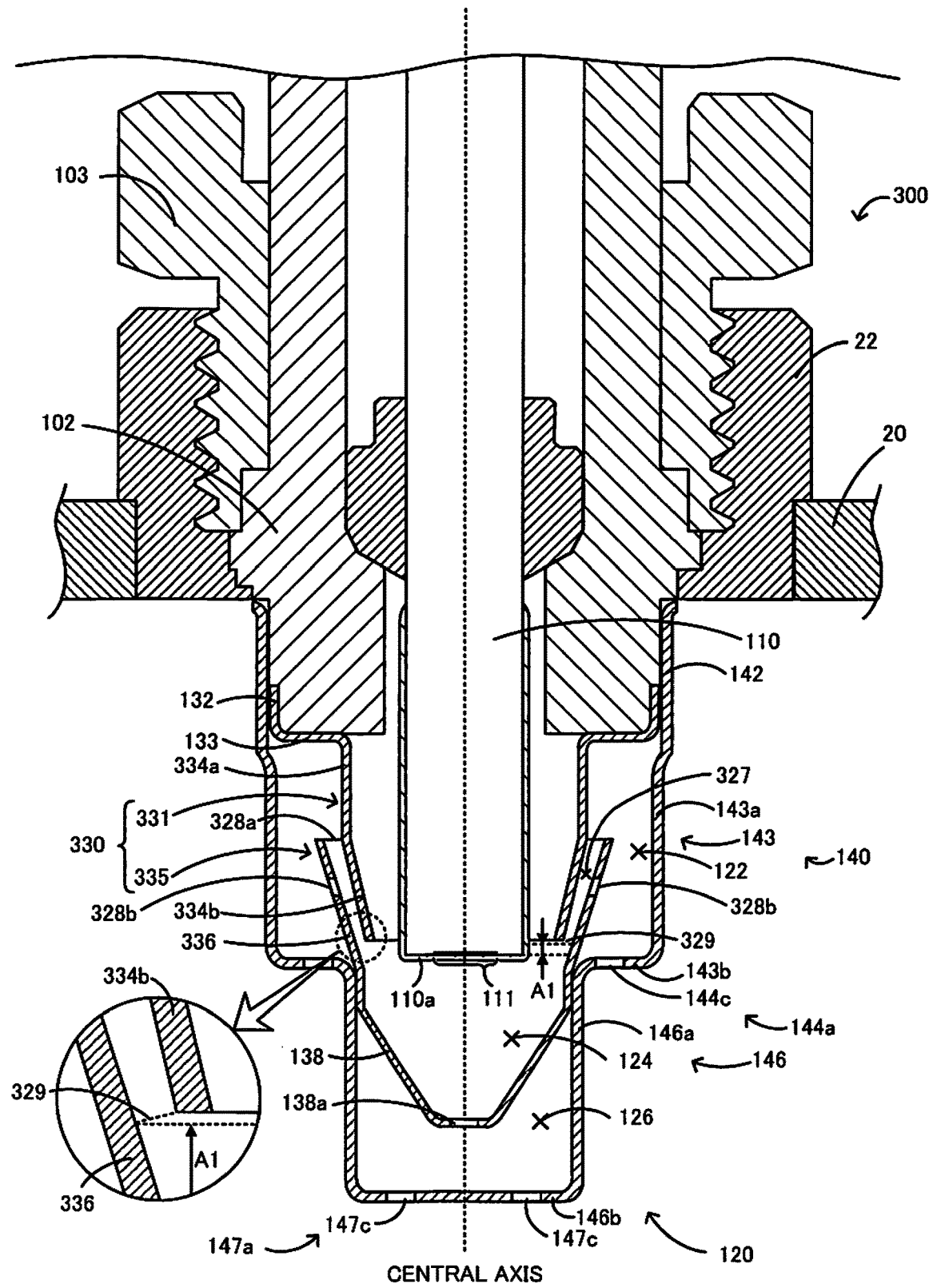
FIG. 16 is a vertical cross-sectional view of a gas sensor 300 according to a modification.

Although the element-chamber inlet 127 includes a flow passage parallel to the back-front direction of the sensor element 110 (i.e., a flow passage parallel to the up-down direction in FIG. 3) in the embodiment described above, the configuration is not limited to this. For example, the element-chamber inlet may include a flow passage that is inclined with respect to the back-front direction such that the flow passage becomes closer to the sensor element 110 with increasing distance from the back end toward the front end of the sensor element 110. FIG. 16 is a vertical cross-sectional view of a gas sensor 300 according to a modification. In FIG. 16, the same components as those of the gas sensor 100 are denoted by the same reference numerals, and their detailed description will be omitted. As illustrated in FIG. 16, the gas sensor 300 includes an inner protective cover 330, instead of the inner protective cover 130. The inner protective cover 330 includes a first member 331 and a second member 335. Unlike the first member 131, the first member 331 does not have the first cylindrical portion 134 and has, instead, a cylindrical barrel portion 334a and a first cylindrical portion 334b in the shape of a cylinder having a diameter gradually reduced from the back side toward the front side of the sensor element 110. The first cylindrical portion 334b is connected to the barrel portion 334a at an end portion thereof on the back side of the sensor element 110. Unlike the second member 135, the second member 335 does not have the second cylindrical portion 136 and the connecting portion 137 and has, instead, a second cylindrical portion 336 in the shape of a cylinder having a diameter gradually reduced from the back side toward the front side of the sensor element 110. The second cylindrical portion 336 is connected to the end portion 138. The outer periphery of the first cylindrical portion 334b and the inner periphery of the second cylindrical portion 336 are not in contact, and a element-chamber inlet 327 includes a gap formed by both of them. The element-chamber inlet 327 has a first outside opening 328a serving as an opening of the gap adjacent to the first gas chamber 122, and an element-side opening 329 serving as an opening of the gap adjacent to the sensor element chamber 124. The element-chamber inlet 327 also has a plurality of (only two of them are shown in FIG. 16) second outside openings 328b which are horizontal holes each allowing, in the gap between the outer periphery of the first cylindrical portion 334b and the inner periphery of the second cylindrical portion 336, the path of the measurement-object gas from the first outside opening 328a to the element-side opening 329 to communicate in the middle thereof with the first gas chamber 122. In the gas sensor 300 illustrated in FIG. 16, the length of the shortest path of the measurement-object gas extending from the outer inlet 144a through the second outside opening 328b to the gas inlet 111 is shorter than the length of the shortest path of the measurement-object gas extending from the outer inlet 144a through the first outside opening 328a to the gas inlet 111. Thus, as in the embodiment described above, the loss of responsiveness when the measurement-object gas flows at low velocity can be reduced. Also, the element-chamber inlet 327 includes a flow passage that is inclined with respect to the back-front direction of the sensor element 110, in accordance with the shapes of the first cylindrical portion 334b and second cylindrical portion 336, such that the flow passage becomes closer to the sensor element 110 (i.e., closer to the central axis of the inner protective cover 330) with increasing distance from the back end toward the front end of the sensor element 110. Similarly, the element-side opening 329 opens in a direction inclined with respect to the back-front direction such that it becomes closer to the sensor element 110 with increasing distance from the back end toward the front end of the sensor element 110 (see the enlarged view in FIG. 16). As described above, when the element-chamber inlet 327 includes an inclined flow passage or the element-side opening 329 opens in an inclined direction, the direction in which the measurement-object gas flows from the element-side opening 329 into the sensor element chamber 124 is inclined with respect to the back-front direction of the sensor element 110. Therefore, the same effect as that achieved with the element-chamber inlet 127 and the element-side opening 129 according to the embodiment described above can be achieved. That is, it is possible to prevent the measurement-object gas from perpendicularly hitting the surface (except the gas inlet 111) of the sensor element 110, and also to prevent the measurement-object gas from traveling a long distance over the surface of the sensor element 110 to reach the gas inlet 111. It is thus possible to reduce cooling of the sensor element 110. In FIG. 16, the width of the element-chamber inlet 327 decreases with increasing distance from the back end toward the front end of the sensor element 110. Accordingly, the opening area of the element-side opening 329 is smaller than the opening area of the first outside opening 328a. In other words, in the element-chamber inlet 327, the distance A4 described with reference to FIG. 7 is smaller than the distance A5. This means that when the measurement-object gas flows in through the first outside opening 328a and flows out through the element-side opening 329, the flow velocity of the measurement-object gas that flows out is higher than the flow velocity of the measurement-object gas that flows in. Responsiveness in gas concentration detection can thus be improved. When the measurement-object gas flows in through the second outside opening 328b and flows out through the element-side opening 329, the flow velocity of the measurement-object gas that flows out is also higher than the flow velocity of the measurement-object gas that flows in, and thus the same effect as above can be achieved. In FIG. 16, the element-chamber inlet 327 includes a flow passage inclined with respect to the back-front direction of the sensor element 110, the element-side opening 329 opens in a direction inclined with respect to the back-front direction of the sensor element 110, and the opening area of the element-side opening 329 is smaller than the opening area of the first outside opening 328a. However, one or more of these three characteristics may be omitted, or the gas sensor may be configured to have one or more of these three characteristics. Note, as illustrated in FIG. 16, that the distance A1 in the gas sensor 300 according to the modification is a distance from the gas inlet 111 to the lower end of the element-side opening 329 in the up-down direction.

Although the flow passage of the measurement-object gas between the outer inlet 144a and the element-chamber inlet 127 includes only the first gas chamber 122 in the embodiment described above, the configuration is not limited to this. It is only necessary that the first gas chamber 122 be at least part of the flow passage of the measurement-object gas between the outer inlet 144a and the element-chamber inlet 127. For example, the protective cover 120 may include not only the inner protective cover 130 and the outer protective cover 140, but also an intermediate protective cover disposed therebetween, and thus the flow passage of the measurement-object gas between the outer inlet 144a and the element-chamber inlet 127 may include a plurality of gas chambers. Similarly, although the flow passage of the measurement-object gas between the outer outlet 147a and the element-chamber outlet 138a includes only the second gas chamber 126 in the embodiment described above, the configuration is not limited to this. It is only necessary that the second gas chamber 126 be at least part of the flow passage of the measurement-object gas between the outer outlet 147a and the element-chamber outlet 138a.

Although the gas inlet 111 opens to the front end face (i.e., lower face in FIG. 3) of the sensor element 110 in the embodiment described above, the configuration is not limited to this. For example, the gas inlet 111 may open to a side face of the sensor element 110 (i.e., the upper, lower, right, or left face of the sensor element 110 in FIG. 4).

Although the sensor element 110 has the porous protective layer 110a thereon in the embodiment described above, the sensor element 110 does not necessarily need to have the porous protective layer 110a.

EXAMPLES

Gas sensors specifically made will now be described as examples. Experimental Example 2 corresponds to an example of the present invention, and Experimental Example 1 corresponds to a comparative example. The present invention is not limited to the example described below.

Experimental Example 1

A gas sensor used as Experimental Example 1 is the same as the gas sensor 100 illustrated in FIGS. 3 to 7, except that the outer inlets 144a include six horizontal holes 144b and six vertical holes 144c, the outer outlets 147a include three horizontal holes 147b formed in the side portion 146a and three vertical holes 147c, and the element-chamber inlet 127 does not have the second outside openings 128b as illustrated in FIGS. 12 and 13. Specifically, the first member 131 of the inner protective cover 130 is 0.3 mm in thickness and 10.2 mm in length in the axial direction. The large-diameter portion 132 is 1.8 mm in length in the axial direction and 14.4 mm in outside diameter. The first cylindrical portion 134 is 8.4 mm in length in the axial direction and 7.88 mm in inside diameter. The second member 135 is 0.3 mm in thickness and 11.5 mm in length in the axial direction. The second cylindrical portion 136 is 4.5 mm in length in the axial direction and 9.7 mm in inside diameter. The end portion 138 is 4.9 mm in length in the axial direction and 3.0 mm in diameter at the bottom thereof. For the element-chamber inlet 127, the distance A1 is 0.59 mm, the distance A2 is 2.1 mm, the distance A3 is 3.1 mm, the distances A4, A5, and A7 are each 0.61 mm, and the length L1 is 4 mm. The element-chamber outlet 138a is 1.5 mm in diameter. The outer protective cover 140 is 0.4 mm in thickness and 24.35 mm in length in the axial direction. The large-diameter portion 142 is 5.85 mm in length in the axial direction and 15.2 mm in outside diameter. The barrel part 143 is 8.9 mm in length in the axial direction (i.e., the length from the upper end of the barrel part 143 to the upper face of the step portion 143b in the axial direction is 8.5 mm) and is 14.6 mm in outside diameter. The front end portion 146 is 9.6 mm in length in the axial direction and 8.7 mm in outside diameter. The outer inlets 144a include six horizontal holes 144b and six vertical holes 144c having a diameter of 1 mm and alternately and evenly spaced (i.e., an angle formed between adjacent holes is 30°). The outer outlets 147a include three horizontal holes 147b and three vertical holes 147c having a diameter of 1 mm and alternately and evenly spaced (i.e., an angle formed between adjacent holes is 60°). The protective cover 120 is made of SUS301S. The sensor element 110 of the gas sensor 100 is 4 mm in width (or length in the right-left direction in FIG. 4) and 1.5 mm in thickness (or length in the up-down direction in FIG. 4). The porous protective layer 110a is formed of an alumina porous body and is 400 μm in thickness. The shortest first path length P1 is 11.7 mm.

Experimental Example 2

The gas sensor 100 illustrated in FIGS. 3 to 11 was used as Experimental Example 2. In Experimental Example 2, the outer inlets 144a do not include the horizontal holes 144b, and the vertical holes 144c are 1 mm in diameter, which is the same as that in Experimental Example 1. In Experimental Example 2, the outer outlets 147a do not include the horizontal holes 147b, and the vertical holes 147c are 1 mm in diameter, which is the same as that in Experimental Example 1. The distance A3 between the first outside opening 128a and the vertical hole 144c is 4.9 mm. The distance A6 between the second outside opening 128b and the vertical hole 144c is 1.1 mm. The length L1 is 4.3 mm and the length L2 is 0.5 mm. The other dimensions are the same as those in Experimental Example 1. The shortest first path length P1 is 13.1 mm, and the shortest second path length P2 is 6.7 mm.

(Evaluation of Responsiveness)

For the gas sensors of Experimental Examples 1 and 2, responsiveness in gas concentration detection of the sensor element was evaluated. First, the gas sensor of Experimental Example 1 was attached to a pipe as in FIGS. 1 and 2. Note that the gas sensor of Experimental Example 1 was attached in an orientation which allows the measurement-object gas in the pipe to flow from left to right in FIG. 12. A gas adjusted to have a given oxygen concentration by mixing oxygen and air was used as a measurement-object gas, which was flowed through the pipe at a flow velocity V=8 m/s. Then, how the output of the sensor element changed with time when the concentration of oxygen in the measurement-object gas flowing through the pipe was changed from 22.9% to 20.2% was measured. The output value of the sensor element immediately before the change in oxygen concentration is defined as 0%, and the stabilized output value of the sensor element after the change in oxygen concentration is defined as 100%. Then, the time elapsed from when the output value exceeds 10% to when the output value exceeds 90% is defined as response time (sec) of gas concentration detection. The shorter the response time, the higher the responsiveness in gas concentration detection. The response time was measured multiple times for different orientations of attachment of the gas sensor of Experimental Example 1. Specifically, the gas sensor orientation which allows the measurement-object gas to flow from left to right in FIG. 8 was defined as 0°. Then, the gas sensor was rotated about the central axis of the outer protective cover 140 to change the orientation of the gas sensor from 0° to 360° in steps of 30°, and the response time for each orientation of the gas sensor was measured. Note that 0° and 360° represent the same orientation of the gas sensor. The response time was measured multiple times for the same orientation of the gas sensor. When the concentration of oxygen in the measurement-object gas flowing through the pipe was changed from 20.2% to 22.9% (i.e., which is the reverse of the above-described change in oxygen concentration), the orientation of the gas sensor was changed from 0° to 360° and the response time for the same orientation was measured multiple times, in the same manner as above. Then, the average of all the response times was defined as the response time at the flow velocity V=8 m/s in Experimental Example 1. The same was carried out for Experimental Example 2. That is, the response time was measured multiple times for each of different orientations of the gas sensor attached to the pipe and different directions of change in oxygen concentration, and the average of all the response times was defined as the response time at the flow velocity V=8 m/s in Experimental Example 2. In Experimental Example 2, the gas sensor orientation which allows the measurement-object gas to flow from left to right in FIG. 4 was defined as 0°.

For Experimental Examples 1 and 2, the response time for each of flow velocities V=1 m/s, 2 m/s, 4 m/s, 6 m/s, and 10 m/s was also measured in the same manner as above. Note however that the response times for these velocities were measured when, without changing the orientation of the gas sensor, the concentration of oxygen in the measurement-object gas flowing in the pipe was reduced (or changed from 22.9% to 20.2%) and increased (or changed from 20.2% to 22.9%), and then the average value was defined as the response time corresponding to each flow velocity V. The orientations of the gas sensor in Experimental Examples 1 and 2 were 0° and 30°, respectively.

Figure 17:
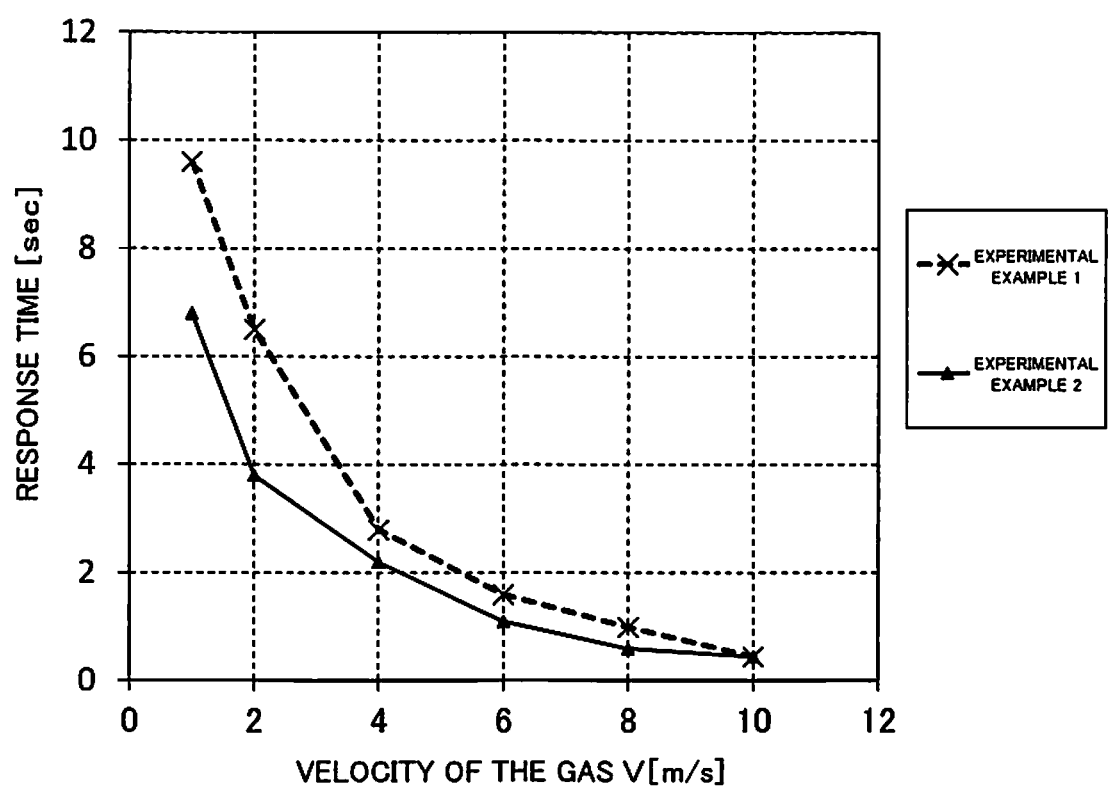
FIG. 17 is a graph showing a relation between flow velocity V and response time in Experimental Examples 1 and 2.

For Experimental Examples 1 and 2, the diameters and numbers of the outer inlets and outer outlets in the outer protective cover, the presence or absence of the second outside openings 128b, and the response time for each flow velocity V are shown in Table 1. FIG. 17 is a graph showing a relation between the flow velocity V and the response time in Experimental Examples 1 and 2.

TABLE 1

| | Outer Protective Cover | | Second Outside Opening | Response Time (Velocity 1 m/s) [sec] | Response Time (Velocity 2 m/s) [sec] | Response Time (Velocity 4 m/s) [sec] | Response Time (Velocity 6 m/s) [sec] | Response Time (Velocity 8 m/s) [sec] | Response Time (Velocity 10 m/s) [sec] |
|---|---|---|---|---|---|---|---|---|---|
| | Outer Inlet | Outer Outlet | | | | | | | |
| Experimental Example 1 | Diameter of 1 mm × 6 (Horizontal Holes) Diameter of 1 mm × 6 (Vertical Holes) | Diameter of 1 mm × 3 (Horizontal Holes) Diameter of 1 mm × 3 (Vertical Holes) | Absent | 9.6 | 6.5 | 2.8 | 1.6 | 1 | 0.45 |
| Experimental Example 2 | Diameter of 1 mm × 6 (Vertical Holes) | Diameter of 1 mm × 6 (Vertical Holes) | Present (Diameter of 1 mm × 6) | 6.8 | 3.8 | 2.2 | 1.1 | 0.6 | 0.45 |

As shown in Table 1 and FIG. 17, the response time tends to increase as the flow velocity V decreases in both Experimental Examples 1 and 2. In Experimental Example 2 having the second outside openings 128b, however, the response time is shorter than that in Experimental Example 1 at low flow velocities V (4 m/s or less). Regardless of the flow velocity V, the response time in Experimental Example 2 having the first outside opening 128a and the second outside openings 128b does not exceed that in Experimental Example 1.

The present application claims priority from Japanese Patent Application No. 2016-121005, filed on Jun. 17, 2016, the entire contents of which are incorporated herein by reference.

What is claimed is:

1. A gas sensor comprising:
a sensor element having a tip end, a rear end opposite the tip end, and a gas inlet through which a measurement-object gas is introduced into the sensor element, the sensor element being configured to detect a concentration of a predetermined gas in the measurement-object gas that has flowed through the gas inlet into the sensor element;
an inner protective cover covering the tip end of the sensor element and containing a sensor element chamber therein having the tip end of the sensor element and the gas inlet disposed therein, the inner protective cover having at least one element-chamber inlet serving as an entrance to the sensor element chamber; and
an outer protective cover having at least one outer inlet serving as an entrance for the measurement-object gas from the outside, the outer protective cover being disposed outside the inner protective cover, wherein:
the outer protective cover and the inner protective cover form a first gas chamber as a space therebetween, the first gas chamber being at least part of a flow passage of the measurement-object gas between the at least one outer inlet and the at least one element-chamber inlet,
each of the at least one element-chamber inlet is a gas flow channel extending from an element-side end to an outer end in a direction from the tip end toward the rear end of the sensor element, each of the at least one element-chamber inlet having: a first outside opening that opens to the first gas chamber and is located at the outer end of the gas flow channel, an element-side opening that opens to the sensor element chamber and is located at the element-side end of the gas flow channel, and a second outside opening disposed such that a path of the measurement-object gas from the first outside opening to the element-side opening communicates in the middle thereof with the first gas chamber and that there is a path shorter than the shortest path of the measurement-object gas extending from the at least one outer inlet through the first outside opening to the gas inlet,
the inner protective cover comprises a first cylindrical portion having a first diameter and a second cylindrical portion having a second diameter that is larger than the first diameter, the second cylindrical portion disposed around the first cylindrical portion such that a gap is formed between the first and second cylindrical portions, and
the element-chamber inlet includes the gap formed between the first and second cylindrical portions.

2. The gas sensor according to claim 1, wherein the second outside opening does not open toward a region extending from the at least one outer inlet.

3. The gas sensor according to claim 1, wherein:
the outer protective cover includes a cylindrical barrel part having a side portion and a bottom portion,
the at least one outer inlet includes a vertical hole disposed in the bottom portion of the barrel part of the outer protective cover, and
when the vertical hole, the second outside opening, and a central axis of the outer protective cover are projected onto a plane perpendicular to the central axis, the projected vertical hole and the projected second outside opening do not overlap as viewed in a radial direction of the outer protective cover from the projected central axis.

4. The gas sensor according to claim 1, wherein the outer protective cover includes a cylindrical barrel part having a side portion and a bottom portion, and the side portion does not have the at least one outer inlet.

5. The gas sensor according to claim 1, wherein the inner protective cover forms the at least one element-chamber inlet such that the element-side opening opens in a direction from the rear end toward the tip end of the sensor element.

6. The gas sensor according to claim 1, wherein:
the first cylindrical portion surrounds the sensor element,
the first cylindrical portion and the second cylindrical portion form the first outside opening as an opening of the gap formed between the first and second cylindrical portions, the opening being adjacent to the first gas chamber, and form the element-side opening as an opening of the gap adjacent to the sensor element chamber, and the second cylindrical portion has the second outside opening that allows the cylindrical gap to communicate with the first gas chamber.

7. The gas sensor according to claim 1, wherein:

the inner protective cover has at least one element-chamber outlet serving as an exit from the sensor element chamber, the outer protective cover has at least one outer outlet serving as an exit for the measurement-object gas to the outside, and the outer protective cover and the inner protective cover form a second gas chamber as a space therebetween, the second gas chamber being at least part of a flow passage of the measurement-object gas between the at least one outer outlet and the at least one element-chamber outlet, the second gas chamber not directly communicating with the first gas chamber.

8. The gas sensor according to claim 7, wherein:

the outer protective cover includes a cylindrical barrel part having the at least one outer inlet, and a tip end portion having the outer outlet, formed in the shape of a cylinder with a bottom, and smaller in inside diameter than the barrel part, the tip end portion being located in a direction from the rear end toward the tip end of the sensor element with respect to the barrel part, and the outer protective cover and the inner protective cover form the first gas chamber as a space between the barrel part of the outer protective cover and the inner protective cover, and form the second gas chamber as a space between the tip end portion of the outer protective cover and the inner protective cover.

* * * * *